(12) United States Patent
Takii et al.

(10) Patent No.: US 10,264,967 B2
(45) Date of Patent: Apr. 23, 2019

(54) SUBJECTIVE OPTOMETRY APPARATUS AND SUBJECTIVE OPTOMETRY PROGRAM

(71) Applicant: NIDEK CO., LTD., Gamagori, Aichi (JP)

(72) Inventors: Michihiro Takii, Nukata (JP); Masaaki Hanebuchi, Nukata (JP); Noriji Kawai, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 15/694,235

(22) Filed: Sep. 1, 2017

(65) Prior Publication Data

US 2018/0064339 A1 Mar. 8, 2018

(30) Foreign Application Priority Data

Sep. 5, 2016 (JP) .................................. 2016-173089
Sep. 5, 2016 (JP) .................................. 2016-173090
Mar. 31, 2017 (JP) .................................. 2017-069850

(51) Int. Cl.
*A61B 3/18* (2006.01)
*A61B 3/00* (2006.01)
(Continued)

(52) U.S. Cl.
CPC .............. *A61B 3/18* (2013.01); *A61B 3/0008* (2013.01); *A61B 3/0025* (2013.01);
(Continued)

(58) Field of Classification Search
CPC ........... A61B 3/0008; A61B 3/14; A61B 3/12; A61B 3/102; A61B 3/0025
(Continued)

(56) References Cited

U.S. PATENT DOCUMENTS

| 3,874,774 A | 4/1975 | Humphrey | |
|---|---|---|---|
| 2012/0162606 A1* | 6/2012 | Nakamura | ............. A61B 3/032 351/221 |
| 2018/0078135 A1* | 3/2018 | Takii | .................... A61B 3/0025 |

FOREIGN PATENT DOCUMENTS

| CN | 101224103 A | 7/2008 |
|---|---|---|
| JP | H05-176893 A | 7/1993 |
| JP | H07-194545 A | 8/1995 |

OTHER PUBLICATIONS

Feb. 6, 2018 Partial European Search Report issued in European Patent Application No. EP 17189377.9.
(Continued)

*Primary Examiner* — Mohammed A Hasan
(74) *Attorney, Agent, or Firm* — Oliff PLC

(57) ABSTRACT

A subjective optometry apparatus includes subjective measurement unit for subjectively measuring an optical characteristic of a subject eye, the subjective measurement unit including a calibration optical system that is disposed in an optical path of a light projecting optical system projecting a visual target luminous flux toward the subject eye and changes an optical characteristic of the visual target luminous flux. The subjective optometry apparatus includes objective measurement unit for objectively measuring the optical characteristic of the subject eye, the objective measurement unit including a measurement optical system that emits measurement light to a fundus of the subject eye and receives reflected light of the measurement light. The subjective optometry apparatus includes controller for objectively measuring the optical characteristic of the subject eye by the objective measurement unit while the optical characteristic of the subject eye is subjectively measured by the subjective measurement unit.

13 Claims, 6 Drawing Sheets

(51) Int. Cl.
  *A61B 3/02* (2006.01)
  *A61B 3/10* (2006.01)
(52) U.S. Cl.
  CPC .............. *A61B 3/0091* (2013.01); *A61B 3/02* (2013.01); *A61B 3/10* (2013.01); *A61B 3/1005* (2013.01); *A61B 2560/0233* (2013.01)
(58) Field of Classification Search
  USPC ........................................................ 351/221
  See application file for complete search history.

(56) References Cited

OTHER PUBLICATIONS

May 11, 2018 Extended European Search Report issued in European Patent Application No. 17189377.9.

\* cited by examiner

SUBJECTIVE OPTOMETRY APPARATUS AND SUBJECTIVE OPTOMETRY PROGRAM

BACKGROUND

The present disclosure relates to a subjective optometry apparatus that subjectively measures an optical characteristic of a subject eye, and a subjective optometry program.

In recent years, for example, there has been known a subjective optometry apparatus which is configured such that calibration optical systems capable of calibrating refractivity are individually disposed in front of an examinee's eyes, and is configured to project an examination visual target onto the fundus of the subject eye through the calibration optical system (see JP-A-5-176893). An examiner receives the examinee's response and adjusts the calibration optical systems until the visual target is appropriately seen by the examinee to thereby obtain a calibration value, and measures a refractive power of the subject eye based on the calibration value. In addition, for example, there has been known a subjective optometry apparatus which is configured such that an image of an examination visual target through a calibration optical system is formed in front of an examinee's eye, and is configured to measure a refractive power of the subject eye without disposing the calibration optical system in front of the eye (U.S. Pat. No. 3,874,774).

SUMMARY

Incidentally, in the subjective optometry apparatus, an optical characteristic of the subject eye may change due to the working of an adjustment function of the subject eye, or the like while the optical characteristic of the subject eye is subjectively measured. In a case where subjective measurement is performed in such a state where the optical characteristic changes, it is difficult to measure the optical characteristic of the subject eye with a high level of accuracy.

This disclosure is contrived in view of such a problem, and an object thereof is to provide a subjective optometry apparatus capable of measuring an optical characteristic of a subject eye with a high level of accuracy when the optical characteristic of the subject eye is subjectively measured.

In order to solve the above-described problem, the invention includes the following configurations.

A subjective optometry apparatus that subjectively measures an optical characteristic of a subject eye, the subjective optometry apparatus comprising:

a light projecting optical system configured to project a visual target luminous flux toward the subject eye;

a subjective measurement unit configured to subjectively measure the optical characteristic of the subject eye, the subjective measurement unit including a calibration optical system that is disposed in an optical path of the light projecting optical system and is configured to change an optical characteristic of the visual target luminous flux;

an objective measurement unit for objectively measure an optical characteristic of the subject eye, the objective measurement unit including a measurement optical system configured to emit measurement light to a fundus of the subject eye and receive the measurement light reflected from the subject eye; and a controller configured to objectively measure the optical characteristic of the subject eye by the objective measurement unit while the optical characteristic of the subject eye is being subjectively measured by the subjective measurement unit.

A subjective optometry apparatus for subjectively measuring an optical characteristic of a subject eye, the subjective optometry apparatus comprising:

a light projecting optical system configured to project a visual target luminous flux toward the subject eye;

a subjective measurement unit for subjectively measuring the optical characteristic of the subject eye, the subjective measurement unit including a calibration optical system that is disposed in an optical path of the light projecting optical system and is configured to change an optical characteristic of the visual target luminous flux;

an objective measurement unit for objectively measuring the optical characteristic of the subject eye, the objective measurement unit including a measurement optical system configured to emit measurement light to a fundus of the subject eye and receive the measurement light reflected from the subject eye;

a controller for:
objectively measuring the optical characteristic of the subject eye by the objective measurement unit to acquire a first optical characteristic; and
objectively measuring the optical characteristic of the subject eye by the objective measurement unit to acquire a second optical characteristic at a timing different from a timing when the first optical characteristic is acquired;

an acquisition unit for acquiring adjustment information based on the first optical characteristic and the second optical characteristic; and an output unit for outputting the adjustment information.

A non-transitory computer readable recording medium storing a program for a subjective optometry apparatus including a light projecting optical system configured to project a visual target luminous flux toward a subject eye, a subjective measurement unit that is configured to subjectively measure an optical characteristic of the subject eye and includes a calibration optical system that is disposed in an optical path of the light projecting optical system and configured to change an optical characteristic of the visual target luminous flux, and an objective measurement unit that is configured to objectively measure the optical characteristic of the subject eye and includes a measurement optical system that emits measurement light to a fundus of the subject eye and receives the measurement light reflected from the subject eye, and subjectively measuring the optical characteristic of the subject eye, the program being executed by a processor of the subjective optometry apparatus to cause the subjective optometry apparatus to execute:

a control step of objectively measuring the optical characteristic of the subject eye by the objective measurement unit while the optical characteristic of the subject eye is being subjectively measured by the subjective measurement unit.

DESCRIPTION OF ILLUSTRATIVE EMBODIMENTS

Figure 1:
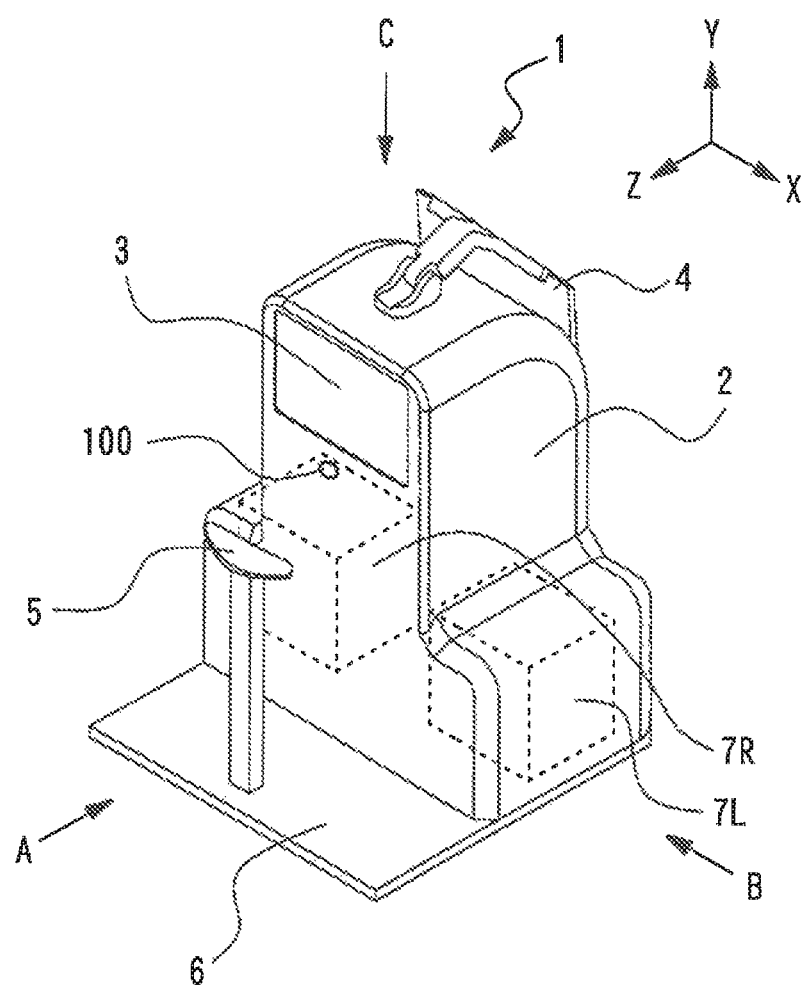
FIG. 1 is a diagram illustrating an exterior of a subjective optometry apparatus.

Hereinafter, one of typical embodiments will be described with reference to the accompanying drawings. FIGS. 1 to 7 are diagrams illustrating a subjective optometry apparatus and a subjective optometry program according to this embodiment. In the following description, an example of the subjective optometry apparatus will be described. Items classified as the following sign "< >" may be used independently of or in relation to each other.

This disclosure is not limited to the apparatus described in this embodiment. For example, terminal control software (program) for performing the function of the following embodiment is supplied to a system or an apparatus through a network, any of various storage mediums, or the like. A control device (for example, a CPU or the like) of the system or the apparatus can also read out and execute a program.

In the following description, a description will be given on the assumption that a depth direction (a front-back direction of an examinee when the examinee is measured) of the subjective optometry apparatus is a Z-direction, a horizontal direction on a plane which is perpendicular (a right-left direction of the examinee when the examinee is measured) to the depth direction is an X-direction, and a vertical direction (an up-down direction of the examinee when the examinee is measured) is a Y-direction. R and L attached to reference numerals are assumed to be signs for the right eye and the left eye, respectively.

<Outline>

For example, the subjective optometry apparatus (for example, a subjective optometry apparatus 1) in this embodiment includes subjective measurement unit. In addition, for example, the subjective optometry apparatus includes objective measurement unit. In addition, for example, the subjective optometry apparatus includes controller (for example, a control section 70).

<Subjective Measurement Unit>

For example, the subjective measurement unit subjectively measures an optical characteristic of a subject eye. Examples of the optical characteristic of the subject eye which is subjectively measured include an eye refractive power (for example, a spherical power, an astigmatic power, an astigmatic axis angle, and the like), a contrast sensitivity, binocular vision function (for example, the amount of oblique position, a stereoscopic function, and the like), and the like.

For example, the subjective measurement unit includes a light projecting optical system (for example, a light projecting optical system 30). In addition, for example, the light projecting optical system projects a visual target luminous flux toward the subject eye. In addition, for example, the subjective measurement unit includes a calibration optical system (for example, a calibration optical system 60 and a subjective measurement optical system 25). For example, the calibration optical system is disposed in an optical path of the light projecting optical system, and changes an optical characteristic of the visual target luminous flux. The light projecting optical system is not required to be integrally provided in the subjective measurement unit, and a configuration may also be adopted in which an apparatus including a light projecting optical system is separately provided. That is, the subjective measurement unit in this embodiment may be configured to include at least a calibration optical system.

<Light Projecting Optical System>

For example, the light projecting optical system includes a light source that projects a visual target luminous flux. In addition, for example, the light projecting optical system may include at least one or more optical members that guide the visual target luminous flux projected from the light source projecting the visual target luminous flux toward a subject eye.

For example, a configuration may also be adopted in which a display (for example, a display 31) is used as the light source that projects the visual target luminous flux. For example, a liquid crystal display (LCD), an organic electroluminescence (EL), or the like is used as the display. For example, an examination visual target such as a Landolt ring visual target is displayed on the display.

For example, a light source and a digital micromirror device (DMD) may be used as the light source that projects the visual target luminous flux. In general, the DMD has high reflectivity and luminance. For this reason, it is possible to maintain the amount of light of the visual target luminous flux as compared to a case where a liquid crystal display using polarization is used.

For example, the light source projecting the visual target luminous flux may be configured to include a visual target presentation visible light source and a visual target plate. In this case, for example, the visual target plate is a rotatable disc plate, and includes a plurality of visual targets. The plurality of visual targets include, for example, a visual target for examination of visual acuity which is used during subjective measurement, and the like. For example, regarding the visual target for examination of visual acuity, a visual target (visual acuity value 0.1, 0.3, . . . , 1.5) is provided for each visual acuity value. For example, the visual target plate is rotated by a motor or the like, and the visual targets are disposed in a switching manner on an optical path through which the visual target luminous flux is guided to the subject eye. Naturally, a light source other than the light source having the above-described configuration may be used as the light source projecting the visual target luminous flux.

<Calibration Optical System>

For example, the calibration optical system may be configured to change an optical characteristic (for example, at least any one of a spherical power, a cylindrical power, a cylindrical axis, a polarization characteristic, the amount of aberration, and the like) of a visual target luminous flux. For example, as a configuration in which the optical characteristic of the visual target luminous flux is changed, a configuration in which an optical element is controlled may be adopted. For example, as the optical element, a configuration may also be adopted in which at least any one of a spherical lens, a cylindrical lens, a cross cylinder lens, a rotary prism, a wavefront modulation element, and the like is used. Naturally, for example, as the optical element, an optical element different from the optical element having the above-described configuration may be used.

For example, the calibration optical system may be configured such that a spherical power of a subject eye is calibrated by a presentation position (presenting distance) of a visual target with respect to an examinee's eye is optically changed. In this case, for example, as a configuration in which the presentation position (presenting distance) of the visual target is optically changed, a configuration may be adopted in which a light source (for example, display) is moved in an optical axis direction. In addition, in this case, for example, a configuration may also be adopted in which the optical element (for example, a spherical lens) which is disposed in the optical path is moved in the optical axis direction. Naturally, the calibration optical system may have a configuration constituted by a configuration in which the optical element is controlled and a configuration in which the optical element disposed in the optical path is moved in the optical axis direction.

For example, the calibration optical system may be an optometry unit (phoropter) in which optical elements disposed in front of a subject eye are disposed in a switching manner. For example, the optometry unit may be configured to include a lens disc having a plurality of optical elements disposed on the same circumference thereof and a driver for rotating the lens disc, and to electrically switch the optical elements by the driving of the driver (for example, a motor).

For example, the calibration optical system may be configured to change an optical characteristic of a visual target luminous flux by disposing an optical element between an optical member for guiding the visual target luminous flux toward the subject eye from the light projecting optical system and a visual target presentation unit and by controlling the optical element. That is, the calibration optical system may have a configuration of a phantom lens refractometer (phantom calibration optical system). In this case, for example, the visual target luminous flux calibrated by the calibration optical system is guided to the subject eye through the optical member.

<Objective Measurement Unit>

For example, the subjective optometry apparatus in this embodiment includes an objective measurement unit. For example, the objective measurement unit objectively measures an optical characteristic of a subject eye. Examples of the optical characteristic of the subject eye which is objectively measured include an eye refractive power (for example, a spherical power, an astigmatic power, an astigmatic axis angle, and the like), a polarization characteristic, thickness information of a crystalline lens, and the like. In this embodiment, an example of the objective measurement unit measuring an eye refractive power of the subject eye will be described. For example, the objective measurement unit includes a measurement optical system (for example, an objective measurement optical system 10) that emits measurement light to the fundus of the subject eye and receives the reflected light thereof. For example, the optical characteristic of the subject eye which is objectively measured may be at least any one of an image capture result (captured image) which is imaged by the objective measurement unit and a parameter which is acquired by analyzing and processing the image capture result. That is, the optical characteristic of the subject eye which is objectively measured may be an optical characteristic based on the image capture result imaged by the objective measurement unit.

For example, the objective measurement unit may include a right subject eye measurement optical system and a left subject eye measurement optical system which are provided on the right and left sides, respectively, as a pair. In this case, for example, the right subject eye measurement optical system and the left subject eye measurement optical system may be configured to execute measurement on the right side and measurement on the left side at substantially the same time. In addition, in this case, for example, measurement by the right subject eye measurement optical system and measurement by the left subject eye measurement optical system may be performed at different timings. For example, the different timings may be timings when the measurement of either the right subject eye measurement optical system or the left subject eye measurement optical system is completed. In addition, for example, the different timings may be during the measurement of either the right subject eye measurement optical system or the left subject eye measurement optical system.

In addition, for example, the objective measurement unit may be configured such that the measurement of the right subject eye and the measurement of the left subject eye are performed by one measurement optical system. In this case, for example, a configuration may also be adopted in which in a case where measurement light is emitted to the fundus of one subject eye to measure the subject eye and the measurement of one eye is completed, adjustment is performed so that measurement light can be emitted to the fundus of the other subject eye, thereby measuring the other subject eye.

<Measurement Optical System>

For example, the measurement optical system includes a light projecting optical system that projects measurement light from a light source toward an examinee's fundus, and an image capture optical system that images reflected light, acquired by the reflection of the measurement light from the fundus, by the image capture element. For example, the measurement optical system may be an optical system that measures an eye refractive power of a subject eye. In this case, examples of a configuration of the measurement optical system include a configuration in which a spot-shaped measurement index is projected onto the subject eye's fundus through a pupil central portion of the subject eye, fundus reflected light reflected from the fundus is taken out in the form of a ring through a pupil peripheral portion, and a ring-shaped fundus reflected image is captured by the image capture element. In addition, in this case, examples of a configuration of the measurement optical system include a configuration in which a ring-shaped measurement index is projected onto the fundus from the pupil peripheral portion, the fundus reflected light is taken out from the pupil central portion, and the ring-shaped fundus reflected image is captured by the image capture element. In addition, in this case, for example, the measurement optical system may be configured to include a Shack Hartman sensor. In addition, in this case, for example, the measurement optical system may be configured to have a phase difference scheme in which a slit is projected onto the subject eye.

<Acquisition of Objective Measurement Result During Subjective Measurement>

In this embodiment, for example, controller objectively measures an optical characteristic of a subject eye by the objective measurement unit while the optical characteristic of the subject eye is being subjectively measured by the subjective measurement unit. For example, when the optical characteristic of the subject eye is objectively measured by the objective measurement unit, the subjective measurement of the optical characteristic of the subject eye by the subjective measurement unit may be continued. In addition, for example, when the optical characteristic of the subject eye is objectively measured by the objective measurement unit, the subjective measurement of the optical characteristic of the subject eye by the subjective measurement unit may be temporarily stopped. In this case, in a case where objective measurement is completed by the objective measurement unit, the subjective measurement of the optical characteristic of the subject eye by the subjective measurement unit may be restarted.

For example, in this embodiment, it is possible to capture a change in the optical characteristic of the subject eye during subjective measurement from an objective measurement result by adopting a configuration in which the optical characteristic of the subject eye is objectively measured by the objective measurement unit while the optical characteristic of the subject eye is being subjectively measured by the subjective measurement unit. Thereby, the examiner can perform subjective measurement taking the change in the optical characteristic of the subject eye during subjective measurement into consideration. For this reason, the examiner can measure the optical characteristic of the subject eye with a high level of accuracy when the optical characteristic of the subject eye is subjectively measured.

For example, as a case where the optical characteristic of the subject eye is objectively measured by the objective measurement unit while the optical characteristic of the subject eye is being subjectively measured by the subjective measurement unit, the controller may objectively measure the optical characteristic of the subject eye by the objective measurement unit while at least one or more subjective examinations are being performed.

For example, at least one or more subjective examinations include a case where one subjective examination is performed and a case where a plurality of subjective examinations are performed. For example, one subjective examination may be an examination for subjectively measuring at least one optical characteristic of the subject eye.

For example, in a case where one subjective examination is performed, the controller may objectively measure the optical characteristic of the subject eye by the objective measurement unit while one subjective examination is being performed by the subjective measurement unit.

For example, in a case where a plurality of subjective examinations are performed, the controller may objectively measure the optical characteristic of the subject eye by the objective measurement unit while one of the plurality of subjective examinations is being performed by the subjective measurement unit. In addition, for example, in a case where a plurality of subjective examinations are performed, the controller may objectively measure the optical characteristic of the subject eye by the objective measurement unit between a first subjective examination and a second subjective examination by the subjective measurement unit. In this case, for example, the first subjective examination and the second subjective examination may be the same subjective examination for measuring an optical characteristic, and the first subjective examination and the second subjective examination may be different subjective examinations for measuring an optical characteristic.

For example, the subjective optometry apparatus may include a transmitter for transmitting an objective measurement start trigger signal for starting objective measurement by the objective measurement unit, and a receiver for receiving the objective measurement start trigger signal. For example, when the objective measurement start trigger signal is transmitted by the transmitter and the objective measurement start trigger signal is received by the receiver, the controller objectively measures the optical characteristic of the subject eye by the objective measurement unit while at least one or more subjective examinations are being performed. For example, the start of objective measurement by the objective measurement unit may be performed manually or automatically.

For example, in a case of a configuration in which the start of objective measurement is manually performed, a start switch is provided as the transmitter for transmitting the objective measurement start trigger signal for starting the objective measurement to the subjective optometry apparatus. For example, the start switch is selected by the examiner, and thus the objective measurement start trigger signal is transmitted. For example, when the objective measurement start trigger signal is received by the receiver, the controller may start measurement by the objective measurement unit. For example, as a configuration in which the optical characteristic of the subject eye is objectively measured by the objective measurement unit during at least one or more subjective examinations, at least one objective measurement may be performed. That is, for example, as a configuration in which the optical characteristic of the subject eye is objectively measured by the objective measurement unit during at least one or more subjective examinations, one objective measurement may be performed as a minimum number of times of measurement, and objective measurement may be performed at all times (in real time) as a maximum number of times of measurement.

For example, in a case where objective measurement is desired to be performed once, the examiner selects the start switch once during at least one or more subjective examinations, and thus the objective measurement may be performed.

In addition, for example, in a case where a plurality of times of objective measurement are desired to be performed, the examiner selects the start switch a plurality of times during at least one or more subjective examinations, and thus the objective measurement may be performed a plurality of times. In addition, for example, in a case where a plurality of times of objective measurement are desired to be performed, the examiner selects the start switch once during at least one or more subjective examinations, and thus the objective measurement may be performed a plurality of times.

For example, in a case where the objective measurement are performed a plurality of times by the objective measurement start trigger signal being output once, the examiner selects the start switch once during at least one or more subjective examinations, and thus the objective measurement may be performed a preset number of times. In addition, for example, in a case where the objective measurement are performed a plurality of times by the objective measurement start trigger signal being output once, the examiner selects the start switch once during at least one or more subjective examinations, and thus the objective measurement may be performed at a preset timing. In addition, for example, in a case where the objective measurement are performed a plurality of times by the objective measurement start trigger signal being output once, the examiner selects the start switch once during at least one or more subjective examinations, and thus the objective measurement may be performed in real time by performing constant measurement.

For example, in a case of a configuration in which the start of objective measurement is automatically performed, the controller controls the transmitter after subjective examination has started, so that the objective measurement start trigger signal is transmitted at a preset timing. For example, when the objective measurement start trigger signal is received by the receiver, the controller may start measurement by the objective measurement unit. In this embodiment, the control of the transmitter is performed by the controller, but the invention is not limited thereto. For example, the control may be performed by separately providing controller different from the controller.

For example, the preset timing may be at least one of a timing when subjective measurement is started (for example, a state where the projection of a visual target luminous flux is started, a state where an examination program is started, a state where the operation of an operation section of a subjective examination apparatus is started, a state where the driving of the calibration optical system is started, and the like), a timing when a preset time has elapsed (for example, when a predetermined time has elapsed from the start of subjective measurement, and the like), a timing when an examination visual target is switched, a timing between subjective examinations (a case where a plurality of subjective examinations are performed), a timing when the examinee makes a response in a subjective examination (a timing when the examiner performs an operation based on the examinee's response), and the like. Naturally, the objective measurement start trigger signal may be output at a timing other than the above-described timings.

For example, as a configuration in which the optical characteristic of the subject eye is objectively measured by the objective measurement unit during at least one or more subjective examinations, at least one objective measurement may be performed. That is, for example, as a configuration in which the optical characteristic of the subject eye is objectively measured by the objective measurement unit during at least one or more subjective examinations, one objective measurement may be performed as a minimum number of times of measurement, and objective measurement may be performed at all times (in real time) as a maximum number of times of measurement.

For example, in a case where objective measurement is desired to be performed once, an objective measurement start trigger may be output at a preset timing during at least one or more subjective examinations, and measurement by the objective measurement unit may be started.

In addition, for example, in a case where objective measurement is desired to be performed a plurality of times, an objective measurement start trigger may be output at a preset timing during at least one or more subjective examinations, and objective measurement may be performed a plurality of times. In this case, for example, the objective measurement may be performed a plurality of times by an objective measurement start trigger signal being output a plurality of times during at least one or more subjective examinations. In this case, for example, the objective measurement may be performed a plurality of times by the objective measurement start trigger signal being output once during at least one or more subjective examinations.

For example, in a case where objective measurement is performed a plurality of times by an objective measurement start trigger signal being output once, an objective measurement start trigger is output once during at least one or more subjective examinations, and thus objective measurement may be performed a preset number of times. In addition, for example, in a case where objective measurement is performed a plurality of times by an objective measurement start trigger signal being output once, the objective measurement may be performed a plurality of times at a preset timing by the objective measurement start trigger being output once during at least one or more subjective examinations. In addition, for example, in a case where objective measurement is performed a plurality of times by the objective measurement start trigger signal being output once, the objective measurement may be performed in real time by performing constant measurement.

<Acquisition of Adjustment Information>

For example, in this embodiment, the controller objectively measures an optical characteristic of a subject eye by the objective measurement unit to acquire a first optical characteristic, and objectively measures an optical characteristic of the subject eye by the objective measurement unit to acquire a second optical characteristic while the optical characteristic of the subject eye is being subjectively measured by the subjective measurement unit.

For example, in this embodiment, the subjective optometry apparatus may include an acquisition unit. For example, in this example, the subjective optometry apparatus may include an output unit. For example, the acquisition unit acquires adjustment information based on the first optical characteristic and the second optical characteristic. For example, the output unit outputs the adjustment information. For example, in this embodiment, the first optical characteristic is acquired by objective measurement, and the second optical characteristic is acquired by objective measurement while the optical characteristic of the subject eye is being subjectively measured. The adjustment information based on the acquired first optical characteristic and second optical characteristic is acquired, and the adjustment information is output. With such a configuration, it is possible to easily acquire a change in the optical characteristic of the subject eye during the subjective measurement from the adjustment information based on the first optical characteristic and the second optical characteristic of the subject eye. For this reason, the examiner can easily measure the optical characteristic of the subject eye with a high level of accuracy when the optical characteristic of the subject eye is subjectively measured using the adjustment information.

For example, as the first optical characteristic and the second optical characteristic at the time of acquiring the adjustment information, it is easier to capture a change in an optical characteristic by using an eye refractive power easily influenced by a change in an adjustment state of the subject eye. Further, in a case where an eye refractive power is used, using at least a spherical power makes it easier to capture a change in an optical characteristic. Naturally, in a case where the eye refractive power is used at the time of acquiring the adjustment information, a configuration in which at least one of a spherical power, an astigmatic power, and an astigmatic axis angle is used may be adopted.

For example, as a timing at which the first optical characteristic is acquired, the first optical characteristic may be acquired before the optical characteristic of the subject eye is subjectively measured by the subjective measurement unit. In this case, for example, the controller may objectively measure the optical characteristic of the subject eye by the objective measurement unit before the optical characteristic of the subject eye is subjectively measured by the subjective measurement unit to acquire the first optical characteristic. For example, in this embodiment, the optical characteristic of the subject eye is objectively measured by the objective measurement unit before the optical characteristic of the subject eye is subjectively measured by the subjective measurement unit. Thereby, since the objective measurement is performed before the subjective measurement of the subjective measurement unit, it is possible to acquire an optical characteristic through objective measurement in a state where a change in an optical characteristic occurring due to using the subjective measurement unit is suppressed. For this reason, it is possible to acquire an optical characteristic through objective measurement in which a change in an optical characteristic is suppressed, and to acquire better adjustment information.

For example, as the timing at which the first optical characteristic is acquired, the first optical characteristic may be acquired after the optical characteristic of the subject eye is subjectively measured by the subjective measurement unit. In this case, for example, the controller may objectively measure the optical characteristic of the subject eye by the objective measurement unit after the subjective measurement of the optical characteristic of the subject eye is completed by the subjective measurement unit, to acquire the first optical characteristic. For example, in this embodiment, after the optical characteristic of the subject eye is subjectively measured by the subjective measurement unit, the optical characteristic of the subject eye is objectively measured by the objective measurement unit. Thereby, since the objective measurement is performed after the subjective measurement of the subjective measurement unit, it is possible to acquire an optical characteristic through objective measurement in a state where a change in an optical characteristic occurring due to using the subjective measurement unit is suppressed. For this reason, it is possible to acquire an optical characteristic through objective measurement in which a change in an optical characteristic is suppressed, and to acquire better adjustment information.

In a case where the first optical characteristic is acquired, fogging may be applied to a subject eye E. For example, in the measurement of an objective eye refractive power in a case of acquiring the first optical characteristic, preliminary measurement of the eye refractive power is performed, and fogging may be applied to the subject eye E based on a result of the preliminary measurement. For example, the preliminary measurement may be measurement of an objective eye refractive power by the objective measurement unit, or may be measurement of a subjective eye refractive power by the subjective measurement unit.

For example, in a case where fogging is applied, fogging may be applied to the subject eye E by the movement of a display 31 in a direction of an optical axis L2. In this case, for example, the display 31 may be moved once to a position where the subject eye E is brought into focus. In addition, for example, in a case where fogging is applied, an optical member (for example, a lens or the like) may be inserted into and removed from an optical path. In addition, for example, in a case where fogging is applied, the optical member (for example, a lens or the like) disposed at the optical path may be switched. For example, after the fogging is applied, the measurement of the eye refractive power for acquiring the first optical characteristic may be performed on the subject eye to which the fogging is applied. In this manner, it is possible to suppress a function of adjusting the subject eye by applying fogging and to acquire the first optical characteristic in a state where the adjustment function is suppressed.

In addition, for example, as the timing at which the first optical characteristic is acquired, the first optical characteristic may be acquired while the optical characteristic of the subject eye is being subjectively measured by the subjective measurement unit. In this case, for example, the first optical characteristic may be acquired while the optical characteristic of the subject eye is being subjectively measured by the subjective measurement unit, and the second optical characteristic may be acquired after the first optical characteristic is acquired.

For example, the adjustment information may be information capable of being compared with the first optical characteristic and the second optical characteristic. For example, the adjustment information may be information acquired by performing differential processing on the first optical characteristic and the second optical characteristic. For example, the adjustment information acquired by performing differential processing may be at least one of a differential result between parameters of the first optical characteristic and the second optical characteristic, a differential image between captured images, and the like. For example, the above-mentioned parameter may be a numerical value of at least one of a spherical power value, an astigmatic power value, an astigmatic axis angle value, and the like.

For example, the differential image may be an image obtained by performing differential processing on a luminance value for each pixel between the captured images. In this case, for example, in a case where there is no change in the first optical characteristic and the second optical characteristic, a luminance value of each pixel in the differential image is 0 (since the captured images are the same image, a difference therebetween is 0). In addition, in this case, for example, in a case where there is a change in the first optical characteristic and the second optical characteristic, a luminance value of each captured image is not 0, and thus an image appears in the differential image.

For example, in a case where differential processing is performed, any optical characteristic can be set as a reference optical characteristic (reference data) for performing the differential processing. For example, the differential result may be acquired by performing differential processing on each optical characteristic with respect to the reference data.

For example, in a case where only the first optical characteristic and the second optical characteristic are acquired, at least one of the first optical characteristic and the second optical characteristic may be set as the reference data. For example, in a case where an optical characteristic is further acquired in addition to the first optical characteristic and the second optical characteristic, any optical characteristic among the acquired optical characteristics may be set as the reference data. For example, in a case where an optical characteristic is set as the reference data, the reference data may be selected by the examiner from a plurality of optical characteristics. In addition, for example, in a case where an optical characteristic is set as the reference data, the reference data may be automatically set by the acquisition unit. In this case, for example, the acquisition unit may set a minimum optical characteristic (the farthest side (side on which the adjustment of an eye is not performed)) among the plurality of optical characteristics as the reference data. In addition, for example, the acquisition unit may set an optical characteristic, acquired immediately before newly acquired reference data, as the reference data among the plurality of optical characteristics. In addition, for example, in a case where a plurality of subjective examinations are performed, the acquisition unit may set any optical characteristic as the reference data from the optical characteristics acquired through objective measurement among the plurality of subjective examinations.

The differential result may be displayed as a numerical value, a graph, or the like. For example, in a case where objective measurement or a plurality of times of objective measurement are performed in real time, differential results thereof may be consecutively displayed. With such a configuration, it is possible to confirm a fluctuation state of an optical characteristic.

For example, it may be determined whether or not the optical characteristic has changed based on at least one of a differential result and a differential image. In this case, for example, a determination unit is provided, and the determination unit may determine whether or not at least one of the differential result, a shape change result of the captured image, and the like satisfies a preset reference and may output the determination result. For example, a result regarding the possibility of being over-calibration may be output as the determination result.

For example, in this embodiment, the adjustment information is acquired through comparison processing, and thus it is possible to more easily acquire a change in the optical characteristic of the subject eye during subjective measurement from the adjustment information having been subjected to the comparison processing. For this reason, the examiner can more easily measure the optical characteristic of the subject eye with a high level of accuracy when the optical characteristic of the subject eye is subjectively measured using the adjustment information.

For example, the adjustment information may be the first optical characteristic and the second optical characteristic. In this case, for example, the adjustment information may be information in which the first optical characteristic and the second optical characteristic are arranged (for example, information in which the first optical characteristic is disposed in a first region and the second optical characteristic is disposed in a second region different from the first region). In addition, in this case, the adjustment information may be information in which the first optical characteristic and the second optical characteristic can be displayed in a switching manner. In addition, in this case, for example, the adjustment information may be information in which the first optical characteristic and the second optical characteristic overlap each other. The superimposed information may be information in which at least portions of the first optical characteristic and the second optical characteristic are superimposed on each other. For example, the adjustment information may be configured such that the above-mentioned pieces of information are performed together.

For example, in this embodiment, the subjective optometry apparatus may include output unit. For example, the output unit outputs adjustment information. For example, the output unit may be configured such that the adjustment information is displayed on a display. In addition, for example, the output unit may be configured to print the adjustment information. For example, the output unit may be configured to transmit the adjustment information toward another apparatus (another controller). In this case, for example, another apparatus receives the adjustment information, and a variety of control may be performed based on the received adjustment information.

In this embodiment, a configuration may also be adopted in which the controller, the acquisition unit (acquisition controller), and the output unit (output controller) may be implemented by one device. In addition, for example, a configuration may also be adopted in which controller, acquisition unit, and output unit are separately provided. Naturally, the above-described each controller may be constituted by a plurality of controller.

In this embodiment, a description has been given of an example of the subjective optometry apparatus that objectively measures an optical characteristic of a subject eye by the objective measurement unit while the optical characteristic of the subject eye is being subjectively measured by the subjective measurement unit, but the invention is not limited thereto. A configuration may also be adopted in which the subjective optometry apparatus can acquire adjustment information. In this case, for example, the controller objectively measures the optical characteristic of the subject eye by the objective measurement unit to acquire the first optical characteristic, and objectively measures the optical characteristic of the subject eye by the objective measurement unit to acquire the second optical characteristic at a timing different from a timing when the first optical characteristic is acquired. For example, the acquisition unit may acquire the adjustment information based on the first optical characteristic and the second optical characteristic. For example, the output unit may output the adjustment information. For example, in this embodiment, the optical characteristic of the subject eye may be objectively measured to acquire the first optical characteristic, and the optical characteristic of the subject eye may be objectively measured by the objective measurement unit to acquire the second optical characteristic at a timing different from a timing when the first optical characteristic is acquired. The adjustment information based on the acquired first optical characteristic and second optical characteristic is acquired, and the adjustment information is output. With such a configuration, the examiner can acquire a change state of the optical characteristic of the subject eye in a case of using the subjective optometry apparatus. Thereby, it is possible to measure the subject eye with a high level of accuracy when the subject eye is measured using the subjective optometry apparatus.

<Correction Processing Based on Adjustment Information>

For example, in this embodiment, the subjective optometry apparatus may include setting controller (for example, the control section 70). For example, in this embodiment, the subjective optometry apparatus may include a first corrector (for example, the control section 70, the calibration optical system 60). For example, the setting controller may set the amount of correction for correcting a change in an adjustment state of a subject eye which occurs while an optical characteristic of the subject eye is being subjectively measured by the subjective measurement unit, based on adjustment information. It is preferable that the amount of correction is set to be the amount of correction by which the occurring change in the adjustment state of the subject eye can be canceled, but the invention is not limited thereto as long as no problem is caused in a subjective examination. For example, the first corrector may perform correction for canceling the change in the adjustment state of the subject eye which occurs due to the subjective measurement unit, based on the amount of correction which is set by the setting controller. For example, in this embodiment, the amount of correction for correcting the change in the adjustment state of the subject eye is set based on the adjustment information, and correction for canceling the change in the adjustment state of the subject eye which occurs due to the subjective measurement unit may be performed based on the amount of correction. Thereby, even when a change in the adjustment state of the subject eye occurs while the optical characteristic of the subject eye is being subjectively measured by the subjective measurement unit, it is possible to perform measurement in a state where the change in the optical characteristic is canceled. Thereby, when the optical characteristic of the subject eye is subjectively measured, it is possible to easily measure the optical characteristic of the subject eye with a high level of accuracy.

For example, regarding the amount of correction, a preset table may be created for each parameter of the adjustment information, and the created table may be stored in a memory (for example, a memory 72). In this case, for example, the setting controller may evoke the amount of correction corresponding to the adjustment state from the memory and may set the amount of correction. In addition, for example, regarding the amount of correction, a computation expression for deriving the amount of correction for each parameter of the adjustment information may be stored in the memory, thereby obtaining the amount of correction using the computation expression.

For example, the first corrector may be configured such that a calibration optical system also serves as the first corrector. For example, in this embodiment, complicated control and separate corrector for canceling the change in the adjustment state are not required by the calibration optical system also serving as the first corrector, and thus it is possible to correct optical aberration with a simple configuration. For example, as the first corrector, dedicated corrector may be separately provided. In this case, for example, the first corrector may be configured to use at least one of a spherical lens, a cylindrical lens, a cross cylinder lens, a rotary prism, a wavefront modulation element, and the like. Naturally, for example, as the first corrector, a member different from the above-described member may be used.

In this embodiment, a configuration may also be adopted in which as the controller, the setting controller (setting controller), and the controller of the first corrector are implemented by one device. In addition, for example, a configuration may also be adopted in which controller, setting controller, and the controller of the first corrector are separately provided. Naturally, the above-described each controller may be constituted by a plurality of controller.

<Correction of Objective Measurement Result Based on Calibration Information of Calibration Optical System>

In this embodiment, for example, the subjective optometry apparatus may be configured such that the calibration optical system is disposed in an optical path of the measurement optical system. Naturally, the subjective optometry apparatus may be configured such that the calibration optical system is not disposed in the optical path of the measurement optical system.

For example, in a case where the calibration optical system is disposed in the optical path of the measurement optical system, the subjective optometry apparatus may include second corrector (for example, the control section 70). For example, the second corrector may correct a measurement result obtained by objectively measuring a subject eye by the objective measurement unit, based on calibration information of the calibration optical system. For example, the second corrector may correct a measurement result obtained by objectively measuring the subject eye by the objective measurement unit so as to cancel a calibration state of the calibration optical system based on the calibration information of the calibration optical system. For example, in this embodiment, in a case where the calibration optical system is present in the optical path of the objective measurement unit, it is possible to correct a deviation of an optical characteristic which occurs due to a measurement luminous flux for objective measurement passing through the calibration optical system. Thereby, even when objective measurement is performed in a case where calibration is performed by the calibration optical system, it is possible to acquire an optical characteristic with a high level of accuracy. For example, when adjustment information based on at least two optical characteristics acquired through the objective measurement is acquired, it may be difficult to perform comparison due to a deviation occurring between the optical characteristics, and thus this technique is more effective.

For example, the second corrector may correct the optical characteristics as a measurement result. In a case where a first optical characteristic and a second optical characteristic are acquired as optical characteristics, at least one of the first optical characteristic and the second optical characteristic may be corrected. In addition, for example, the second corrector may correct the adjustment information as a measurement result.

In this embodiment, a configuration may also be adopted in which the controller and the second corrector (second correction controller) are implemented by one device. In addition, for example, a configuration may also be adopted in which controller and second corrector are separately provided. Naturally, the above-described each controller may be constituted by a plurality of controller.

In this embodiment, a configuration in which an optical characteristic of a subject eye is objectively measured by the objective measurement unit while the optical characteristic of the subject eye is being subjectively measured by the subjective measurement unit may be used for a subjective examination (front spectacle examination) for subjectively measuring the optical characteristic in a state where the subject eye wears spectacles. In this case, for example, in a state where the subject eye wears spectacles, the first optical characteristic may be acquired through objective measurement of the objective measurement unit, and the second optical characteristic objectively measured by the objective measurement unit may be acquired while the optical characteristic of the subject eye is being subjectively measured. In addition, for example, adjustment information based on the acquired first optical characteristic and second optical characteristic may be acquired, and the adjustment information may be output.

For example, in a case where at least one of a differential result and a differential image is obtained as the adjustment information, for example, it may be determined whether or not the optical characteristic has changed based on at least one of the differential result and the differential image. In this case, for example, a result regarding whether being over-calibrated may be output as the determination result. For example, the result regarding whether being over-calibrated is output, and thus it is possible to confirm whether or not the spectacles presently worn are over-calibrated.

For example, as an example, in a state where the subject eye wears spectacles, a visual target for far sight at an infinite distance may be presented to acquire an optical characteristic, and a visual target having a higher degree of lens than the visual target for far sight at an infinite distance may be presented to acquire an optical characteristic. In this case, an adjustment state may be acquired based on the calculated optical characteristics. Thereby, it is possible to confirm whether or not the spectacles presently worn are over-calibrated.

<Setting of Initial Value of Subjective Examination>

In this embodiment, for example, the subjective optometry apparatus may include initial value setting controller (for example, the control section 70). In this case, for example, the controller may start subjective measurement of an optical characteristic of a subject eye by the subjective measurement unit and then may objectively measure the optical characteristic of the subject eye by the objective measurement unit to acquire the optical characteristic of the subject eye. For example, the initial value setting controller may set the optical characteristic of the subject eye which is objectively measured by the controller as an initial value of the calibration optical system when the optical characteristic of the subject eye is subjectively measured by the subjective measurement unit. Examples of the optical characteristic set as the initial value include at least one of a spherical power, a cylindrical power, a cylindrical axis, a polarization characteristic, the amount of aberration, and the like. Naturally, a configuration in which the optical characteristic is set as the initial value, other than the above-described configuration, may be adopted. For example, in this embodiment, after the subjective measurement of the optical characteristic of the subject eye is started by the subjective measurement unit, the optical characteristic of the subject eye is objectively measured by the objective measurement unit to acquire the optical characteristic of the subject eye. The optical characteristic of the subject eye which is objectively measured is set as an initial value of the calibration optical system when the optical characteristic of the subject eye is subjectively measured by the subjective measurement unit. With such a configuration, it is not necessary to wait for the subjective measurement of the subjective examination apparatus until the objective measurement is completed, and thus it is possible to rapidly measure the optical characteristic of the subject eye.

For example, the start of the subjective measurement may refer to a state where the control of the subjective measurement is started. In more detail, for example, the start of the subjective measurement may refer to at least one of a state where the projection of a visual target luminous flux is started, a state where an examination program is started, a state where the operation of an operation section of the subjective examination apparatus is started, a state where the driving of the calibration optical system is started, and the like.

For example, the initial value setting controller may be configured to set the optical characteristic of the subject eye which is objectively measured, as an initial value in a subjective examination performed at the time of starting the objective measurement as a subjective examination to be set as an initial value. In this case, for example, the initial value setting controller sets the optical characteristic of the subject eye which is objectively measured by the objective measurement unit, as an initial value of the calibration optical system in the subjective measurement of the optical characteristic of the subject eye which is performed by the subjective measurement unit before the objective measurement of the objective measurement unit is started. For example, in this embodiment, the optical characteristic of the subject eye which is objectively measured by the objective measurement unit is set as an initial value of the calibration optical system in the subjective measurement of the optical characteristic of the subject eye which is performed by the subjective measurement unit before the objective measurement of the objective measurement unit is started. With such a configuration, it is possible to rapidly perform the subjective measurement of the subjective examination apparatus.

In addition, for example, the initial value setting controller may be configured to set the optical characteristic of the subject eye which is objectively measured as an initial value in a subjective examination (second subjective examination) different from the subjective examination (first subjective examination) which is performed when the objective measurement is started, as a subjective examination to be set as an initial value. In this case, for example, the controller may execute first subjective measurement for subjectively measuring an optical characteristic of a subject eye by the subjective measurement unit, and then may execute second subjective measurement for subjectively measuring an optical characteristic of a subject eye by the subjective measurement unit again. For example, the controller may start the first subjective measurement and then may objectively measure the optical characteristic of the subject eye by the objective measurement unit. For example, the initial value setting controller may set the optical characteristic of the subject eye which is objectively measured by the objective measurement unit as an initial value of the second subjective measurement. For example, in this embodiment, the first subjective measurement for subjectively measuring an optical characteristic of a subject eye by the subjective measurement unit is executed, and then the second subjective measurement for subjectively measuring an optical characteristic of a subject eye by the subjective measurement unit is executed again. After the first subjective measurement is started, the optical characteristic of the subject eye is objectively measured by the objective measurement unit, and the optical characteristic of the subject eye which is objectively measured is set as the initial value of the second subjective measurement. With such a configuration, even when subjective measurement is performed again, an initial value is already acquired during different subjective measurement, and thus it is possible to rapidly perform measurement.

For example, the first subjective examination may be a subjective examination for measuring the same optical characteristic as the optical characteristic which is measured through the second subjective examination. In addition, for example, the first subjective examination may be a subjective examination for measuring an optical characteristic different from the optical characteristic which is measured through the second subjective examination. In this case, for example, the first subjective examination may be a subjective examination (naked eye examination) for subjectively measuring an optical characteristic in a case of a naked subject eye. In addition, for example, the first subjective examination may be a subjective examination (front spectacle examination) for subjectively measuring an optical characteristic in a state where a subject eye wears spectacles. In these cases, for example, the first subjective measurement is a subjective measurement for subjectively measuring an optical characteristic of a subject eye in a non-calibration state where an optical characteristic of a visual target luminous flux is not changed by the calibration optical system, and the second subjective measurement may be a subjective measurement for subjectively measuring an optical characteristic of a subject eye by changing an optical characteristic of a visual target luminous flux by the calibration optical system.

In this embodiment, the subjective optometry apparatus may be configured to use a visual target luminous flux of the light projecting optical system as a fixation target to be fixedly viewed by a subject eye when an optical characteristic of the subject eye is objectively measured by the objective measurement unit. For example, in this embodiment, a visual target luminous flux of a light projecting optical system in the subjective detector is set to be a fixation target to be fixedly viewed by a subject eye when an optical characteristic of the subject eye is objectively measured by the objective measurement unit. With such a configuration, it is possible to reduce the number of members and to constitute the apparatus with a simple configuration. In addition, it is possible to reduce extra space and to reduce the size of the apparatus.

In this embodiment, a configuration may also be adopted in which the controller and the initial value setting controller (initial value setting controller) are implemented by one device. In addition, for example, a configuration may also be adopted in which controller and initial value setting controller are separately provided. Naturally, the above-described each controller may be constituted by a plurality of controller.

EXAMPLE

Hereinafter, the subjective optometry apparatus of this example will be described. For example, FIG. 1 is a diagram illustrating the exterior of the subjective optometry apparatus 1 according to this example. For example, the subjective optometry apparatus 1 in this example includes a housing 2, a presentation window 3, an operation section (monitor) 4, a chin mount 5, a base 6, an image capture optical system 100, and the like. For example, the housing 2 accommodates members therein. For example, the housing 2 includes measurement unit (a dotted line portion in FIG. 1) 7 therein (details thereof will be described later). For example, the measurement unit 7 includes right eye measurement unit (right eye measurement unit) 7R and left eye measurement unit (left eye measurement unit) 7L. In this embodiment, the right eye measurement unit 7R and the left eye measurement unit 7L include the same member. That is, the subjective optometry apparatus 1 includes a pair of right and left subjective measurement unit and a pair of right and left objective measurement unit. Naturally, the right eye measurement unit 7R and the left eye measurement unit 7L may be configured such that at least portions of the members thereof are different from each other.

For example, the presentation window 3 is used to present a visual target to an examinee. For example, visual target luminous flux from the right eye measurement unit 7R and the left eye measurement unit 7L is projected onto the subject eye E through the presentation window 3.

For example, the monitor (display) 4 is a touch panel. That is, in this embodiment, the monitor 4 functions as an operation section (controller). The monitor 4 outputs a signal based on an input operation instruction to the control section 70 to be described later. Naturally, the monitor 4 and the operation section may be configured to be separately provided. For example, the operation section may be configured to use at least one operation device such as a mouse, a joystick, or a keyboard.

For example, the monitor 4 may be a display mounted on the main body of the subjective optometry apparatus 1, or may be a display connected to the main body of the subjective optometry apparatus 1. Naturally, the monitor may not be a touch panel type monitor. For example, a display of a personal computer (hereinafter, referred to as a "PC") may be used as the monitor. In addition, for example, a plurality of displays may be used together. For example, a measurement result is displayed on the monitor 4.

For example, the chin mount 5 is used to keep a distance between the subject eye E and the subjective optometry apparatus 1 constant or to suppress considerable movement of a face. For example, the chin mount 5 and the housing 2 are fixed to the base 6. In this embodiment, the chin mount 5 is used to keep a distance between the subject eye E and the subjective optometry apparatus 1 constant, but the invention is not limited thereto. A configuration may be adopted in which a distance between the subject eye E and the subjective optometry apparatus 1 is kept constant. Examples of a configuration in which a distance between the subject eye E and the subjective optometry apparatus 1 is kept constant include configurations using a forehead protector, a face protector, and the like.

For example, the image capture optical system 100 is constituted by an image capture element and a lens not shown in the drawing. For example, the image capture optical system is used to capture an image of the face of the subject eye.

<Measurement Unit>

Figure 2:
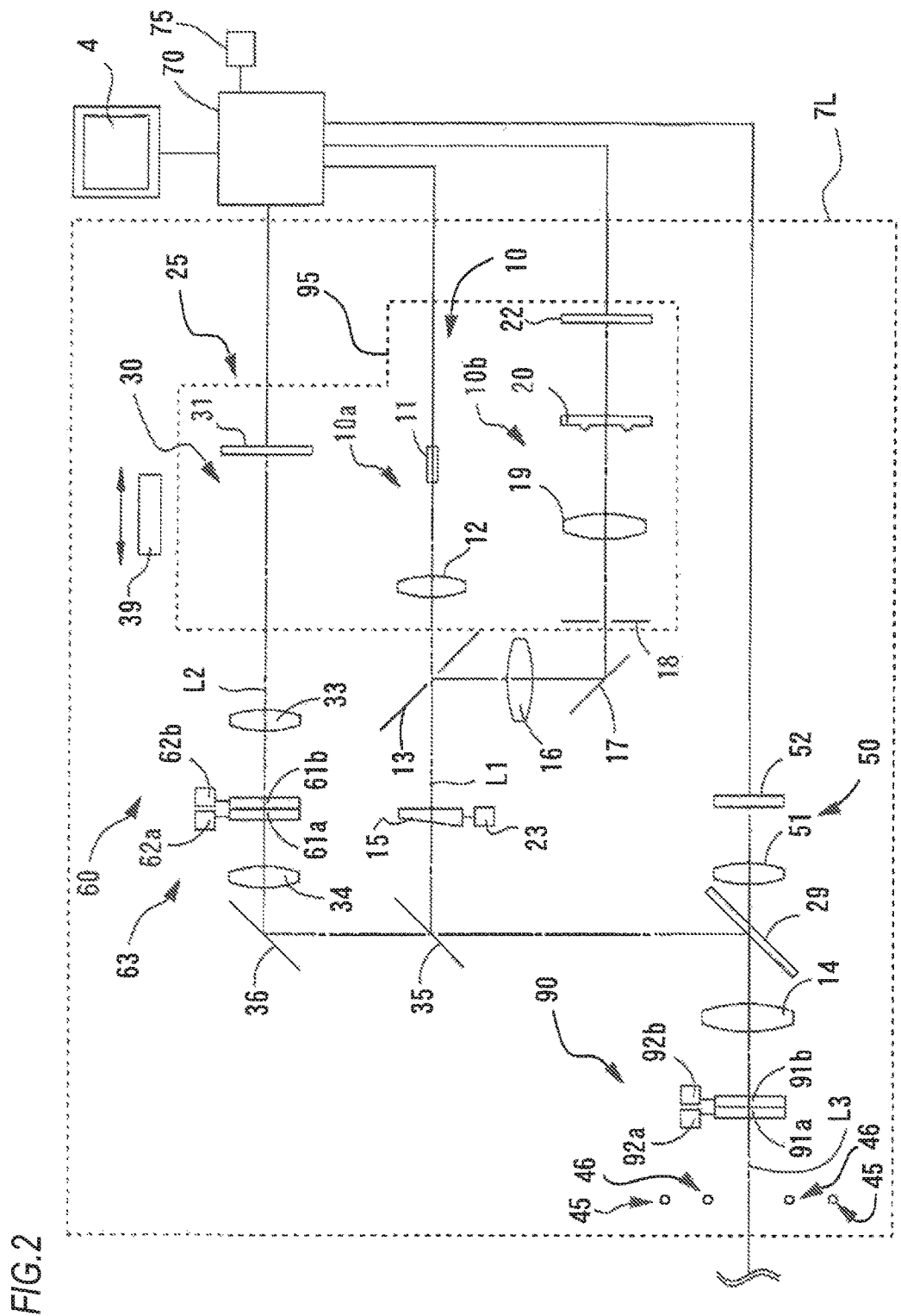
FIG. 2 is a diagram illustrating a configuration of measurement unit.

FIG. 2 is a diagram illustrating a configuration of the measurement unit 7. In this embodiment, an example of the left eye measurement unit 7L is described. In this embodiment, the right eye measurement unit 7R has the same configuration as that of the left eye measurement unit 7L, and thus a description thereof will be omitted. For example, the left eye measurement unit 7L includes the subjective measurement optical system 25, the objective measurement optical system 10, a first index projection optical system 45, a second index projection optical system 46, and an observation optical system 50.

<Subjective Optical System>

For example, the subjective measurement optical system 25 is used as a portion of a configuration of the subjective measurement unit for subjectively measuring an optical characteristic of a subject eye (details thereof will be described later). Examples of the optical characteristic of the subject eye include an eye refractive power, a contrast sensitivity, a binocular vision function (for example, the amount of oblique position, a stereoscopic function, and the like), and the like. In this embodiment, an example of the subjective measurement unit for measuring an eye refractive power of a subject eye will be described. For example, the subjective measurement optical system 25 includes a light projecting optical system (visual target projection system) 30, a calibration optical system 60, and a correction optical system 90.

For example, the light projecting optical system 30 projects a visual target luminous flux toward the subject eye E. For example, the light projecting optical system 30 includes a display 31, a projection lens 33, a projection lens 34, a reflecting mirror 36, a dichroic mirror 35, a dichroic mirror 29, and an objective lens 14. For example, a visual target luminous flux projected from the display 31 is projected onto the subject eye E through an optical member in order of the projection lens 33, the projection lens 34, the reflecting mirror 36, the dichroic mirror 35, the dichroic mirror 29, and the objective lens 14.

For example, an examination visual target such as a Landolt ring visual target, a fixation target (used during objective measurement to be described later, and the like) to be fixedly viewed by the subject eye E, and the like are displayed on the display 31. For example, a visual target luminous flux from the display 31 is projected toward the subject eye E. In this example, the following description will be given using an example of a case where an LCD is used as the display 31.

For example, the calibration optical system 60 includes an astigmatism calibration optical system 63 and a driving mechanism 39.

For example, the astigmatism calibration optical system 63 is disposed between the projection lens 34 and the projection lens 33. For example, the astigmatism calibration optical system 63 is used to calibrate a cylindrical power, a cylindrical axis, and the like of a subject eye. For example, the astigmatism calibration optical system 63 is constituted by two positive cylindrical lenses 61a and 61b having the same focal distance. The cylindrical lenses 61a and 61b are independently rotated about an optical axis L2 by the driving of respective rotation mechanisms 62a and 62b. In this embodiment, the astigmatism calibration optical system 63 has been described using an example of a configuration in which the two positive cylindrical lenses 61a and 61b are used, but the invention is not limited thereto. The astigmatism calibration optical system 63 may be configured to calibrate a cylindrical power, a cylindrical axis, and the like.

For example, a configuration may also be adopted in which a calibration lens is inserted into and removed from an optical path of the light projecting optical system 30.

For example, the display 31 is integrally moved in a direction of the optical axis L2 by the driving mechanism 39 constituted by a motor and a slide mechanism. For example, a presentation position (presenting distance) of a visual target with respect to the examinee's eye is optically changed by the movement of the display 31 during subjective measurement, and thus a spherical refractive power of the subject eye is calibrated. That is, a calibration optical system of a spherical power is configured by the movement of the display 31. In addition, for example, fogging is applied to the subject eye E by the movement of the display 31 during objective measurement. The calibration optical system of the spherical power is not limited thereto. For example, the calibration optical system of the spherical power includes a large number of optical elements, and may be configured to perform calibration by the optical elements being disposed in the optical path. In addition, for example, a configuration may also be adopted in which a lens disposed in the optical path is moved in the optical axis direction.

In this embodiment, an example of the calibration optical system for calibrating a spherical power, a cylindrical power, and a cylindrical axis has been described, but the invention is not limited thereto. For example, a calibration optical system for calibrating a prism value may be provided. The calibration optical system for the prism value is provided, and thus it is possible to perform calibration such that a visual target luminous flux is projected onto a subject eye even when the examinee has heterophoria.

In this embodiment, a description has been given of an example of a configuration in which the astigmatism calibration optical system 63 of the cylindrical power and the cylindrical axis and the calibration optical system (for example, driver 39) of the spherical power are separately provided, but the invention is not limited thereto. For example, the calibration optical system may be configured such that a spherical power, a cylindrical power, and a cylindrical axis are calibrated. For example, the calibration optical system may be an optical system that modulates a wavefront. In addition, for example, the calibration optical system may be an optical system that calibrates a spherical power, a cylindrical power, a cylindrical axis, and the like. In this case, for example, the calibration optical system may be configured to include a lens disc on which a large number of optical elements (a spherical lens, a cylindrical lens, a dispersing prism, and the like) are disposed on the same circumference. The rotation of the lens disc is controlled by a driving section (actuator or the like), and thus the examiner's desired optical element is disposed on the optical axis L2.

In addition, the rotation of the optical element (for example, a cylindrical lens, a cross cylinder lens, a rotary prism, or the like) which is disposed on the optical axis L2 is controlled by the driving section, and thus the optical element is disposed on the optical axis L2 with the examiner's desired rotation angle. The switching of the optical element disposed on the optical axis L2, and the like may be performed by the operation of an input device (operation device) such as the monitor 4.

The lens disc is constituted by one lens disc or a plurality of lens discs. In a case where the plurality of lens discs are disposed, driving sections corresponding to the respective lens discs are provided. For example, as a lens disc group, each lens disc includes an opening (or a lens of 0 D) and a plurality of optical elements. Representative types of lens discs include a spherical lens disc including a plurality of spherical lenses having different powers, a cylindrical lens disc including a plurality of cylindrical lenses having different powers, and an auxiliary lens disc including a plurality of types of auxiliary lenses. At least one of a red filter/green filter, a prism, a cross cylinder lens, a polarizing plate, a Maddox lens, an auto-cross cylinder lens is disposed at the auxiliary lens disc. In addition, the cylindrical lens may be rotatably disposed about the optical axis L2 by the driving section, and the rotary prism and cross cylinder lens may be rotatably disposed about each optical axis by the driving section.

For example, the correction optical system 90 is disposed between the objective lens 14 and a deflection mirror 81 to be described later. For example, the correction optical system 90 is used to correct optical aberration occurring due to the subjective measurement unit. For example, the correction optical system 90 is used to correct astigmatism in the optical aberration. For example, the correction optical system 90 is constituted by two positive cylindrical lenses 91a and 91b having the same focal distance. For example, the correction optical system 90 adjusts a cylindrical power and a cylindrical axis to correct astigmatism. The cylindrical lenses 91a and 91b are independently rotated about an optical axis L3 by the rotation of the respective rotation mechanisms 92a and 92b. In this embodiment, a description has been given of an example of the correction optical system 90 configured to use the two positive cylindrical lenses 91a and 91b, but the invention is not limited thereto. The correction optical system 90 may be configured to be capable of calibrating astigmatism. For example, a configuration may also be adopted in which a correction lens is inserted into and removed from the optical axis L3. In this embodiment, a description has been given of an example of a configuration in which the correction optical system 90 is separately disposed, but the invention is not limited thereto. A configuration may also be adopted in which the calibration optical system 60 also serves as the correction optical system 90. In this case, the cylindrical power and the cylindrical axis of the subject eye are corrected in accordance with the amount of astigmatism. That is, the calibration optical system 60 is driven so as to calibrate the (corrected) cylindrical power and cylindrical axis which take the amount of astigmatism into consideration. In this manner, for example, complicated control and separate correction optical system for optical aberration are not required by the calibration optical system 60 also serving as the correction optical system 90, and thus it is possible to correct optical aberration with a simple configuration.

<Objective Optical System>

For example, the objective measurement optical system 10 is used as a portion of a configuration of the objective measurement unit for objectively measuring an optical characteristic of a subject eye (details thereof will be described later). Examples of the optical characteristic of the subject eye include an eye refractive power, an ocular axial length, a cornea shape, and the like. In this embodiment, an example of the objective measurement unit for measuring an eye refractive power of a subject eye will be described.

For example, the objective measurement optical system 10 includes a projection optical system 10a, a light receiving optical system 10b, and a correction optical system 90. For example, the projection optical system (light projecting optical system) 10a projects a spot-shaped measurement index onto the fundus of the subject eye E through the pupil central portion of the subject eye E. For example, the light receiving optical system 10b extracts fundus reflected light reflected from the fundus in a ring shape through the pupil peripheral portion, and causes a two-dimensional image capture element to capture a ring-shaped fundus reflected image.

For example, the projection optical system 10a includes a measurement light source 11, a relay lens 12, a hole mirror 13, a prism 15, a driving section (motor) 23, a dichroic mirror 35, a dichroic mirror 29, and an objective lens 14 which are disposed on an optical axis L1 of the objective measurement optical system 10. For example, the prism 15 is a luminous flux deflection member. For example, the driving section 23 is a rotation unit for rotating the prism 15 about the optical axis L1. For example, the light source 11 is conjugated with the subject eye fundus, and a hole portion of the hole mirror 13 is conjugated with the pupil. For example, the prism 15 is disposed at a position away from the position conjugated with the pupil of the subject eye E, and a luminous flux to pass through the prism is eccentric with the optical axis L1. A configuration may also be adopted in which a parallel plane plate is obliquely disposed on the optical axis L1 as a luminous flux deflection member instead of the prism 15.

For example, the dichroic mirror 35 is common to the optical path of the subjective measurement optical system 25 and the optical path of the objective measurement optical system 10. That is, for example, the dichroic mirror 35 has the optical axis L2 of the subjective measurement optical system 25 and the optical axis L1 of the objective measurement optical system 10 as the same axis. For example, a beam splitter 29 which is an optical path branching member reflects a luminous flux of the subjective measurement optical system 25 and measurement light of the projection optical system 10a, and guides the reflected luminous flux and measurement light to the subject eye.

For example, the light receiving optical system 10b shares the objective lens 14, the dichroic mirror 29, the dichroic mirror 35, the prism 15, and the hole mirror 13 with the projection optical system 10a, and includes a relay lens 16 and a mirror 17 which are disposed in an optical path in the reflection direction of the hole mirror 13, and a light receiving diaphragm 18, a collimator lens 19, a ring lens 20, and a two-dimensional image capture element 22 (hereinafter, referred to as an image capture element 22) such as a CCD, which are disposed in an optical path in the reflection direction of the mirror 17. For example, the light receiving diaphragm 18 and the image capture element 22 are conjugated with the subject eye fundus. For example, the ring lens 20 is constituted by a lens portion formed in a ring shape and a light shielding portion obtained by performing coating for light shielding on a region other than the lens portion, and has an optically conjugate positional relationship with the pupil of the subject eye. For example, an output from the image capture element 22 is input to a computational control section 70 (hereinafter, a control section 70).

For example, the dichroic mirror 29 reflects reflected light of the measurement light from the projection optical system 10a based on the subject eye fundus toward the light receiving optical system 10. In addition, for example, the dichroic mirror 29 transmits front eye portion observation light and alignment light, and guides the transmitted light to the observation optical system 50. In addition, for example, the dichroic mirror 35 reflects reflected light of the measurement light from the projection optical system 10a based on the subject eye fundus toward the light receiving optical system 10.

The objective measurement optical system 10 is not limited to the above-described objective measurement optical system, and it is possible to use a well-known objective measurement optical system configured to project a ring-shaped measurement index onto the fundus from the pupil peripheral portion, to extract fundus reflected light from the pupil central portion, and to cause the two-dimensional image capture element to receive light of the ring-shaped fundus reflected image.

The objective measurement optical system 10 is not limited to the above-described objective measurement optical system, and may be a measurement optical system including a light projecting optical system that projects measurement light toward an examinee's fundus and a light receiving optical system in which reflected light acquired by the reflection of the measurement light from the fundus is received by a light receiving element. For example, an eye refractive power measurement optical system may be configured to include a Shack Hartman sensor. Naturally, an apparatus using another measurement method may be used (for example, an apparatus of a phase difference system which projects a slit).

For example, the light source 11 of the projection optical system 10a, the light receiving diaphragm 18, the collimator lens 19, the ring lens 20, and the image capture element 22 of the light receiving optical system 10b are configured to be integrally rotatable in the optical axis direction. In this embodiment, for example, the light source 11 of the projection optical system 10a, the light receiving diaphragm 18 of the light receiving optical system 10b, the collimator lens 19, the ring lens 20, and the image capture element 22 of the light receiving optical system 10b are integrally moved in the direction of the optical axis L1 by the driving mechanism 39 that drives the display 31. That is, the display 31, the light source 11 of the projection optical system 10a, the light receiving diaphragm 18 of the light receiving optical system 10b, the collimator lens 19, the ring lens 20, and the image capture element 22 of the light receiving optical system 10b are integrally moved as a driver 95 in synchronization with each other. Naturally, a configuration in which these components are separately driven may also be adopted. For example, the driver 95 moves a portion of the objective measurement optical system 10 in the optical axis direction so that an external ring luminous flux is incident on the image capture element 22 with respect to each longitudinal direction. That is, a portion of the objective measurement optical system 10 is moved in the direction of the optical axis L1 in accordance with a spherical refractive error (spherical refractive power) of the subject eye, so that the spherical refractive error is corrected and the light source 11, the light receiving diaphragm 18, and the image capture element 22 are optically conjugated with the subject eye fundus. The position of the driving mechanism 39 to be moved is detected by a potentiometer not shown in the drawing. The hole mirror 13 and the ring lens 20 are disposed so as to be conjugated with the pupil of the subject eye with a fixed magnification, regardless of the amount of movement of the movable unit 25.

In the above-described configuration, measurement light emitted from the light source 11 forms a spot-shaped point light source image on the fundus of the subject eye through the relay lens 12, the hole mirror 13, the prism 15, the dichroic mirror 35, the beam splitter 29, and the objective lens 14. At this time, a pupil projection image (projected luminous flux on the pupil) of the hole portion of the hole mirror 13 is eccentrically rotated at high speed by the prism 15 rotating around the optical axis. The point light source image projected onto the fundus is reflected and scattered, is emitted to the subject eye, is collected by the objective lens 14, and is collected again at the position of the light receiving diaphragm 18 through the beam splitter 29, the dichroic mirror 35, the prism 15 rotated at high speed, the hole mirror 13, the relay lens 16, and the mirror 17, thereby forming a ring-shaped image on the image capture element 22 by the collimator lens 19 and the ring lens 20.

For example, the prism 15 is disposed at an optical path which is common to the projection optical system 10a and the light receiving optical system 10b. For this reason, a reflected luminous flux from the fundus passes through the prism 15 which is the same as that of the projection optical system 10a, and thus backward scanning is performed as if there is no eccentricity of a projected luminous flux and reflected luminous flux (received luminous flux) on the pupil in the subsequent optical systems.

For example, the correction optical system 90 also serves as the subjective measurement optical system 25. Naturally, a configuration may also be adopted in which a correction optical system used in the objective measurement optical system 10 is separately provided.

<First Index Projection Optical System and Second Index Projection Optical System>

In this embodiment, the first index projection optical system 45 and the second index projection optical system 46 are disposed between the correction optical system 90 and the deflection mirror 81. Naturally, the arrangement position of the first index projection optical system 45 and the second index projection optical system 46 are not limited thereto.

In the first index projection optical system 45, a plurality of infrared light sources are disposed on the concentric circle about the optical axis L3 at intervals of 45 degrees, and are disposed so as to be bilaterally symmetrical to each other with a vertical plane passing through the optical axis L3 therebetween. The first index projection optical system 45 emits near infrared light for projecting an alignment index onto the subject eye's cornea. The second index projection optical system 46 is disposed at a position different from the position of the first index projection optical system 45, and includes six infrared light sources. In this case, the first index projection optical system 45 is configured to project an index at an infinite distance onto the cornea of the examinee's eye E from the right-left direction, and the second index projection optical system 46 is configured to project an index at a finite distance onto the cornea of the examinee's eye E from the up-down direction or an oblique direction. In FIG. 2, only portions of the first index projection optical system 45 and the second index projection optical system 46 are illustrated for convenience of description. The second index projection optical system 46 is also used as an anterior ocular segment illumination that illuminates the subject eye's anterior ocular segment. In addition, the second index projection optical system can also be used as an index for measuring the shape of a cornea. In addition, the first index projection optical system 45 and the second index projection optical system 46 are not limited to a dot-shaped light source. For example, the systems may be a ring-shaped light source or a linear light source.

<Observation Optical System>

The observation optical system (image capture optical system) 50 shares the objective lens 14 and the dichroic mirror 29 in the subjective measurement optical system 25 and the objective measurement optical system 10, and includes an imaging lens 51 and a two-dimensional image capture element 52. For example, the image capture element 52 has an imaging surface disposed at a position substantially conjugated with the subject eye's anterior ocular segment. For example, an output from the image capture element 52 is input to the control section 70. Thereby, an anterior ocular segment image of the subject eye is captured by the two-dimensional image capture element 52 and is displayed on the monitor 4. The observation optical system 50 also serves as an optical system that detects an alignment index image formed on the subject eye's cornea by the first index projection optical system 45 and the second index projection optical system 46, and the position of the alignment index image is detected by the control section 70.

<Internal Configuration of Subjective Optometry Apparatus>

Figure 3:
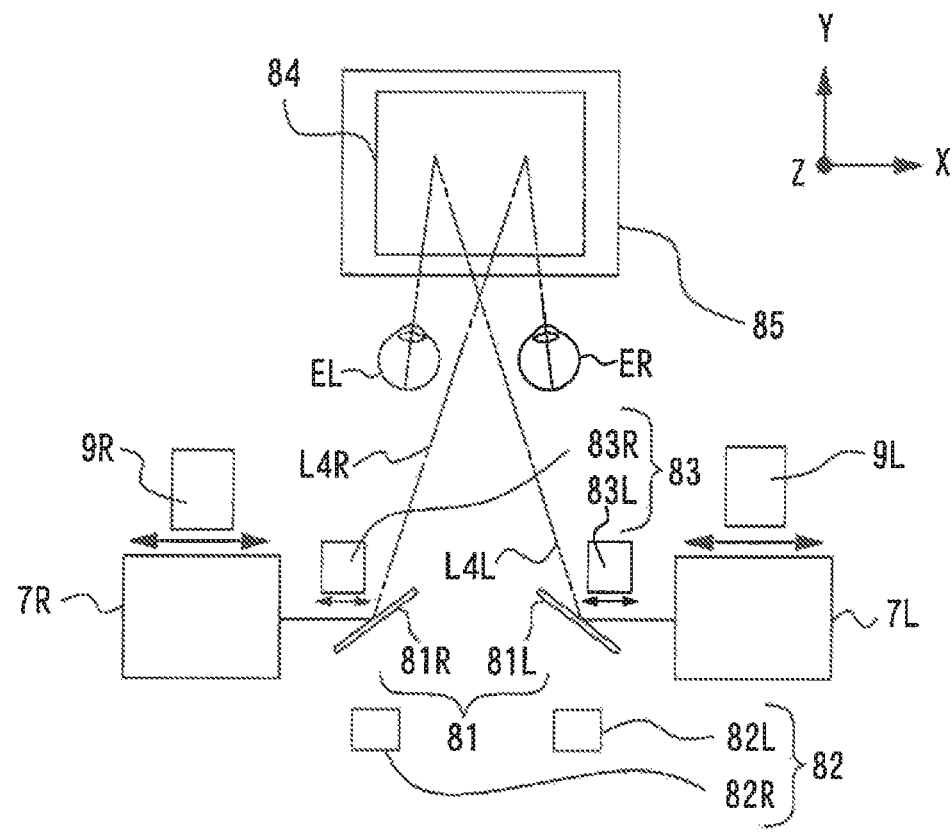
FIG. 3 is a diagram illustrating a schematic configuration when the inside of the subjective optometry apparatus is seen from the front.
Figure 4:
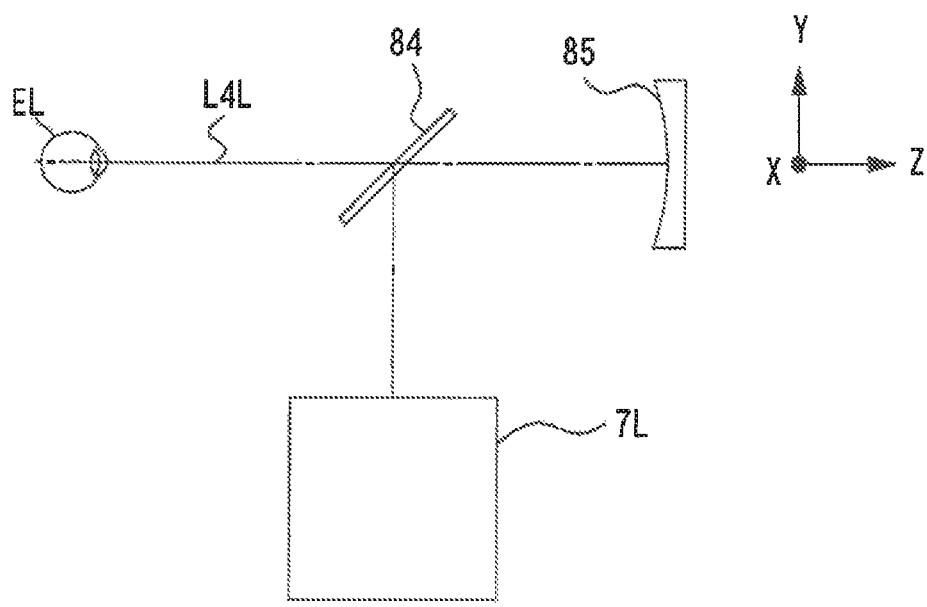
FIG. 4 is a diagram illustrating a schematic configuration when the inside of the subjective optometry apparatus is seen from the side.
Figure 5:
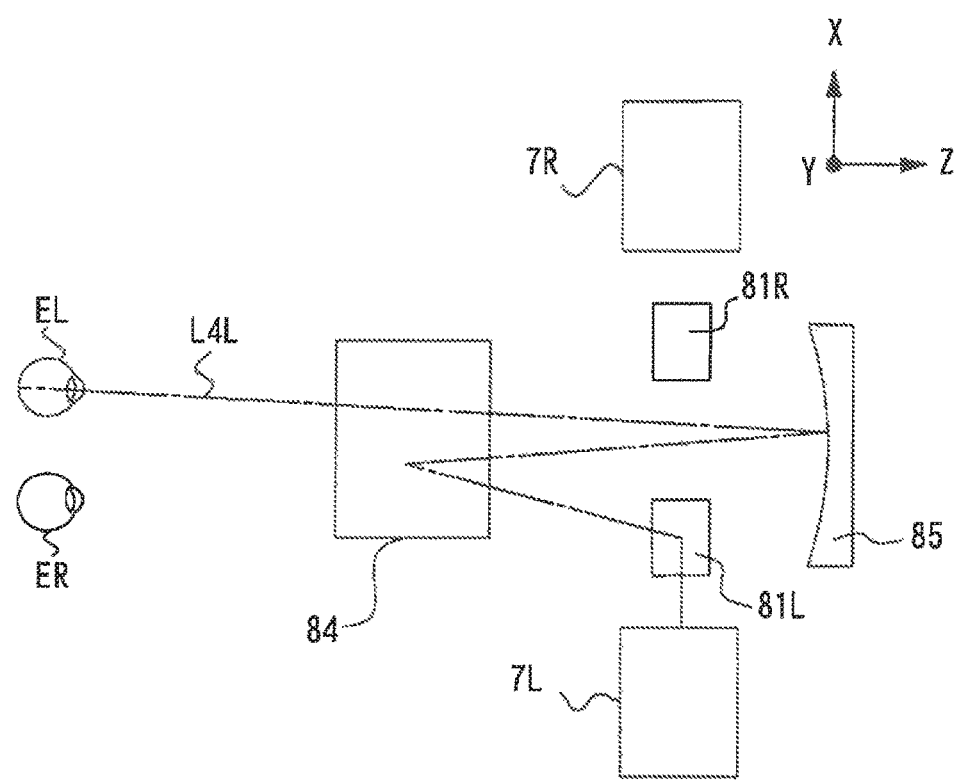
FIG. 5 is a diagram illustrating a schematic configuration when the inside of the subjective optometry apparatus is seen from above.

Hereinafter, the internal configuration of the subjective optometry apparatus 1 will be described. FIG. 3 is a schematic configuration diagram when the inside of the subjective optometry apparatus 1 according to this example is seen from the front (a direction A of FIG. 1). FIG. 4 is a schematic configuration diagram when the inside of the subjective optometry apparatus 1 according to this example is seen from the side (a direction B of FIG. 1). FIG. 5 is a schematic configuration diagram when the inside of the subjective optometry apparatus 1 according to this example is seen from the above (a direction C of FIG. 1). In FIG. 3, an optical axis indicating reflection by a half mirror 84 is omitted for convenience of description. In FIG. 4, only the optical axis of the left eye measurement unit 7L is illustrated for convenience of description. In FIG. 5, only the optical axis of the left eye measurement unit 7L is illustrated for convenience of description.

For example, the subjective optometry apparatus 1 includes subjective measurement unit and objective measurement unit. For example, the subjective measurement unit includes measurement unit 7, a deflection mirror 81, driver 83, driver 82, a half mirror 84, and a concave surface mirror 85. Naturally, the subjective measurement unit is not limited to such a configuration. As an example, the subjective measurement unit may be configured not to include the half mirror 84. In this case, the optical axis of the concave surface mirror 85 may be irradiated with a luminous flux from the oblique direction, and the reflected luminous flux thereof may be guided to the subject eye E. For example, the objective measurement unit includes measurement unit 7, a deflection mirror 81, a half mirror 84, and a concave surface mirror 85. Naturally, the objective measurement unit is not limited to such a configuration. As an example, the objective measurement unit may be configured not to include the half mirror 84. In this case, the optical axis of the concave surface mirror 85 may be irradiated with a luminous flux from the oblique direction, and the reflected luminous flux thereof may be guided to the subject eye E.

The subjective optometry apparatus 1 includes right eye driver 9R and left eye driver 9L, and can move the right eye measurement unit 7R and the left eye measurement unit 7L in the X-direction, respectively. For example, the right eye measurement unit 7R and the left eye measurement unit 7L are moved, and thus a distance between the deflection mirror 81 and the measurement unit 7 is changed, and the presentation position of a visual target luminous flux in the Z-direction is changed. Thereby, it is possible to guide the visual target luminous flux calibrated by the calibration optical system 60 to the subject eye and to perform adjustment in the Z-direction so that an image of the visual target luminous flux calibrated by the calibration optical system 60 is formed on the subject eye's fundus.

For example, the deflection mirror 81 includes a right eye deflection mirror 81R and a left eye deflection mirror 81L which are provided as a pair on right and left sides, respectively. For example, the deflection mirror 81 is disposed between the calibration optical system 60 and the subject eye. That is, the calibration optical system 60 includes a right eye calibration optical system and a left eye calibration optical system which are provided as a pair on right and left sides respectively. The right eye deflection mirror 81R is disposed between the right eye calibration optical system and a right eye ER, and the left eye deflection mirror 81L is disposed between the left eye calibration optical system and a left eye ER. For example, it is preferable that the deflection mirror 81 is disposed at a position conjugated with the pupil.

For example, the right eye deflection mirror 81R reflects a luminous flux projected from the right eye measurement unit 7R, and guides the luminous flux to the right eye ER. In addition, for example, the right eye deflection mirror reflects the reflected light reflected by the right eye ER, and guides the reflected light to the right eye measurement unit 7R. For example, the left eye deflection mirror 81L reflects a luminous flux projected from the left eye measurement unit 7L, and guides the luminous flux to the left eye EL. In addition, for example, the left eye deflection mirror reflects the reflected light reflected by the left eye EL, and guides the reflected light to the left eye measurement unit 7L. In this embodiment, a description has been given of an example of a configuration in which the deflection mirror 81 is used as a deflection member that reflects a luminous flux projected from the measurement unit 7 and guides the luminous flux to the subject eye E, but the invention is not limited thereto. Any deflection member that reflects a luminous flux projected from the measurement unit 7 and guides the luminous flux to the subject eye E may be used. Examples of the deflection member include a prism, a lens, and the like.

For example, the driver 83 is constituted by a motor (driving section), and the like. For example, the driver 83 includes driver 83R for driving the right eye deflection mirror 81R, and driver 83L for driving the left eye deflection mirror 81L. For example, the deflection mirror 81 can be moved in the X-direction by the driving of the driver 83. For example, a distance between the right eye deflection mirror 81R and the left eye deflection mirror 81L is changed by the movement of the right eye deflection mirror 81R and the left eye deflection mirror 81L, and thus it is possible to change a distance between a right eye optical path and a left eye optical path in the X-direction in accordance with a distance between the subject eye and the pupil.

For example, the driver 82 is constituted by a motor (driving section) or the like. For example, the driver 82 includes driver 82R for driving the right eye deflection mirror 81R and driver 82L for driving the left eye deflection mirror 81L. For example, the deflection mirror 81 is rotated by the driving of the driver 82. For example, the driver 82 rotates the deflection mirror 81 about a rotation axis in the horizontal direction (X-direction) and a rotation axis in the vertical direction (Y-direction). That is, the driver 82 rotates the deflection mirror 81 in the XY directions. The rotation of the deflection mirror 81 may be performed in either the horizontal direction or the vertical direction. A configuration may also be adopted in which a plurality of deflection mirrors are provided in each of the right eye optical path and the left eye optical path. Examples of the configuration include a configuration in which two deflection mirrors are provided in each of the right eye optical path and the left eye optical path (for example, two deflection mirrors in the right eye optical path, or the like). In this case, one deflection mirror may be rotated in the X-direction, and the other deflection mirror may be rotated in the Y-direction. For example, the deflection mirror 81 is rotated, and thus it is possible to optically correct the position of an image to be formed by deflecting an apparent luminous flux for the image of the calibration optical system 60 to be formed in front of the subject eye.

For example, the concave surface mirror 85 is shared by the right eye measurement unit 7R and the left eye measurement unit 7L. For example, the concave surface mirror 85 is shared by a right eye optical path including a right eye calibration optical system and a left eye optical path including a left eye calibration optical system. That is, the concave surface mirror 85 is disposed at a position where the concave surface mirror passes through both the right eye optical path including the right eye calibration optical system and the left eye optical path including the left eye calibration optical system. Naturally, the concave surface mirror 85 may be configured not to be shared. A configuration may also be adopted in which the concave surface mirror is provided in each of the right eye optical path including the right eye calibration optical system and the left eye optical path including the left eye calibration optical system. For example, the concave surface mirror 85 guides a visual target luminous flux having passed through the calibration optical system to the subject eye, and forms an image of the visual target luminous flux having passed through the calibration optical system in front of the subject eye. In this embodiment, a configuration in which the concave surface mirror 85 is used has been described as an example, but the invention is not limited thereto. It is possible to use various optical members. Examples of the optical member to be used may include a lens, a planar mirror, and the like.

For example, the concave surface mirror 85 also serves as subjective measurement unit and objective measurement unit. For example, a visual target luminous flux projected from the subjective measurement optical system 25 is projected onto the subject eye through the concave surface mirror 85. In addition, for example, measurement light projected from the objective measurement optical system 10 is projected onto the subject eye through the concave surface mirror 85. In addition, for example, reflected light of the measurement light projected from the objective measurement optical system 10 is guided to the light receiving optical system 10b of the objective measurement optical system 10 through the concave surface mirror 85. In this embodiment, a configuration in which the reflected light of the measurement light from the objective measurement optical system 10 is guided to the light receiving optical system 10b of the objective measurement optical system 10 through the concave surface mirror 85 has been described as an example, but the invention is not limited thereto. A configuration may also be adopted in which the reflected light of the measurement light from the objective measurement optical system 10 does not go through the concave surface mirror 85.

In more detail, for example, in this embodiment, an optical axis between the concave surface mirror 85 and the subject eye E in the subjective measurement unit and an optical axis between the concave surface mirror 85 and the subject eye E in the objective measurement unit are configured as substantially the same axis. In this embodiment, the optical axis L2 of the subjective measurement optical system 25 and the optical axis L1 of the objective measurement optical system 10 are combined with each other by the dichroic mirror 35, and are thus configured as the same axis.

Hereinafter, the optical path of the subjective measurement unit will be described. For example, the subjective measurement unit reflects a visual target luminous flux having passed through the calibration optical system 60 in a direction of the subject eye by the concave surface mirror 85 to thereby guide the visual target luminous flux to the subject eye, and forms an image of the visual target luminous flux having passed through the calibration optical system 60 in front of the subject eye so as to optically have a predetermined examination distance. That is, the concave surface mirror 85 reflects the visual target luminous flux so as to convert the visual target luminous flux into a substantially parallel luminous flux. For this reason, a visual target image seen from the examinee looks as if the visual target image is located farther than the actual distance between the subject eye E and the display 31. That is, the concave surface mirror 85 is used, and thus it is possible to present the visual target image to the examinee so that the image of the visual target luminous flux is seen at the predetermined examination distance.

A more detailed description will be given. In the following description, the left eye optical path will be described as an example. The right eye optical path also has the same configuration as that of the left eye optical path. For example, in the subjective measurement unit for the left eye, a visual target luminous flux projected from the display 31 of the left eye measurement unit 7L is incident on the astigmatism calibration optical system 63 through the projection lens 33. The visual target luminous flux having passed through the astigmatism calibration optical system 63 is incident on the correction optical system 90 through the reflecting mirror 36, the dichroic mirror 35, the dichroic mirror 29, and the objective lens 14. The visual target luminous flux having passed through the correction optical system 90 is projected toward the left eye deflection mirror 81L from the left eye measurement unit 7L. The visual target luminous flux emitted from the left eye measurement unit 7L and reflected by the left eye deflection mirror 81 is reflected toward the concave surface mirror 85 by the half mirror 84. The visual target luminous flux reflected by the concave surface mirror reaches the left eye EL through the half mirror 84.

Thereby, a visual target image calibrated by the calibration optical system 60 based on a spectacle wearing position of the left eye EL (for example, a position separated from the vertex of the cornea at approximately 12 mm) is formed on the fundus of the left eye EL. Therefore, this is equivalent to the arrangement of the astigmatism calibration optical system 63 in front of the eye and the adjustment of a spherical power by a calibration optical system (in this embodiment, driving of the driving mechanism 39) of a spherical power, and thus the examinee can collimate the visual target image in a natural state through the concave surface mirror 85. In this embodiment, the right eye optical path also has the same configuration as that of the left eye optical path, and the visual target image calibrated by a pair of right and left calibration optical systems 60 is formed on the fundi of both subject eyes, based on spectacle wearing positions (for example, positions apart from the vertexes of the corneas at approximately 12 mm) of both the subject eyes ER and EL. In this manner, the examinee responds to the examiner while looking straight at the visual target in a state of a natural sight, attempts calibration by the calibration optical system 60 until an examination visual target is seen properly, and subjectively measures an optical characteristic of the subject eye based on the calibration value thereof.

Subsequently, the optical path of the objective measurement unit will be described. In the following description, the left eye optical path will be described as an example. The right eye optical path also has the same configuration as that of the left eye optical path. For example, in the objective measurement unit for the left eye, measurement light emitted from the light source 11 of the projection optical system 10a in the objective measurement optical system 10 is incident on the correction optical system 90 through the relay lens 12 to the objective lens 14. The measurement light having passed through the correction optical system 90 is projected toward the left eye deflection mirror 81L from the left eye measurement unit 7L. The measurement light emitted from the left eye measurement unit 7L and reflected by the left eye deflection mirror 81 is reflected toward the concave surface mirror 85 by the half mirror 84. The measurement light reflected by the concave surface mirror reaches the left eye EL through the half mirror 84, thereby forming a spot-shaped point light source image on the fundus of the left eye EL. At this time, a pupil projection image (a projected luminous flux on the pupil) of the hole portion of the hole mirror 13 is eccentrically rotated at high speed by the prism 15 rotating about the optical axis.

Light of the point light source image formed on the fundus of the left eye EL is reflected and scattered, and is emitted to the subject eye E, is collected by the objective lens 14 through the optical path through which the measurement light is transmitted, and passes through the dichroic mirror 29, the dichroic mirror 35, the prism 15, the hole mirror 13, the relay lens 16, and the mirror 17. The reflected light having passed through these components from the dichroic mirror to the mirror 17 is collected again on the opening of the light receiving diaphragm 18, is converted into a substantially parallel luminous flux (a case of a normal vision eye) by the collimator lens 19, is extracted as a ring-shaped luminous flux by the ring lens 20, and is received by the image capture element 22 as a ring image. The received ring image is analyzed, and thus it is possible to objectively measure an optical characteristic of the subject eye.

<Control Section>

For example, the control section 70 includes a CPU (processor), a RAM, a ROM, and the like. For example, the CPU of the control section 70 controls each member of the subjective optometry apparatus 1. For example, the RAM temporarily stores various pieces of information. Various programs for controlling the operation of the subjective optometry apparatus 1, visual target data for various examinations, an initial value, and the like are stored in the ROM of the control section 70. The control section 70 may be constituted by a plurality of control sections (that is, a plurality of processors).

For example, a non-volatile memory (storage section) 72, a monitor (also serves as an operation section in this embodiment) 4, various members, and the like are electrically connected to the control section 70. The non-volatile memory (hereinafter, referred to as a memory) 72 is a non-fugitive storage medium capable of holding stored contents even when the supply of power is stopped. For example, a hard disc drive, a flash ROM, an OCT device 1, a USB memory capable of being detachably mounted to the subjective optometry apparatus 1, or the like can be used as the non-volatile memory 72. For example, a control program for controlling the subjective measurement unit and the objective measurement unit is stored in the memory 72.

<Control Operation>

Figure 6:
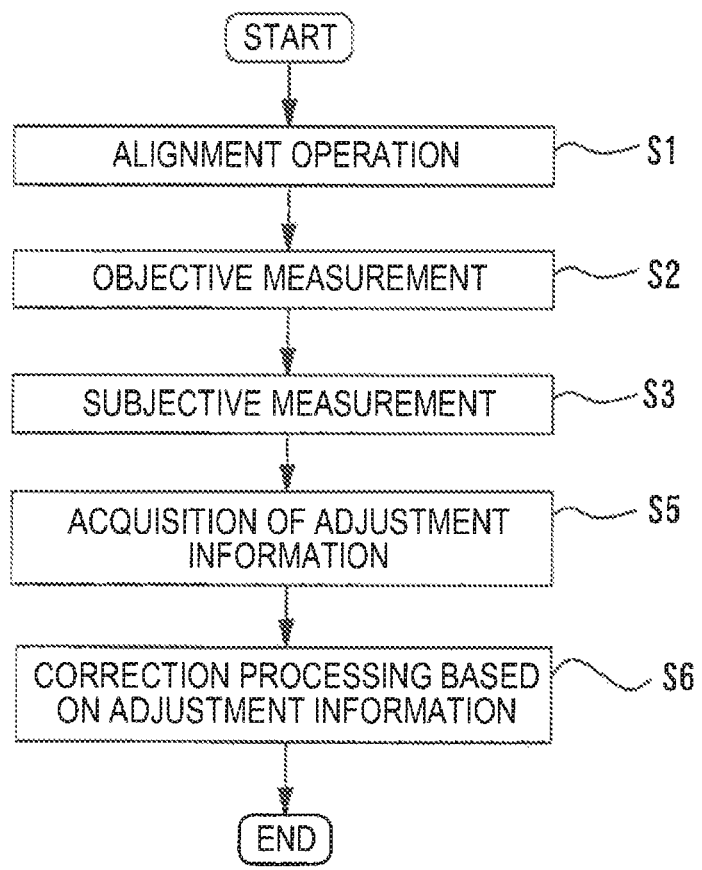
FIG. 6 is a flow chart illustrating a flow of a control operation.

Hereinafter, a control operation of the subjective optometry apparatus 1 will be described. FIG. 6 is a flow chart illustrating a flow of a control operation in this example. The examiner puts the examinee's chin on the chin mount 5 to instruct the examinee to observe the presentation window 3. The examiner instructs the examinee to fixedly view a fixation target displayed on the display 31, and then performs alignment on the subject eye.

<Alignment Operation (S1)>

When an alignment start switch is selected by the examiner, the control section 70 starts automatic alignment (S1). In this example, a case where an optical characteristic of the subject eye during far measurement will be described as an example. Similarly to the far measurement, it is also possible to measure an optical characteristic of the subject eye during near measurement.

For example, the control section 70 detects the position of the pupil of each of the right and left subject eyes from a face image captured by the image capture optical system 100. For example, when the position of the pupil is detected, the control section 70 controls the subjective optometry apparatus 1 so that an anterior ocular segment image is displayed on the monitor 4. For example, the control section 70 respectively drives the right eye deflection mirror 81R and the left eye deflection mirror 81L, and rotates the mirrors in the XY directions. In addition, for example, when the position of the pupil is detected, the control section 70 can move the right eye measurement unit 7R and the left eye measurement unit 7L in the X-direction, respectively. That is, the control section 70 drives the deflection mirror 81 to perform alignment in the XY directions, and drives the measurement unit 7 to perform alignment in the Z-direction.

In this embodiment, a description has been given of an example of a configuration in which alignment in the XYZ directions is adjusted by the driving of the deflection mirror 81 and the measurement unit 7, but the invention is not limited thereto. Any configuration may be adopted as long as a positional relationship between the subject eye, the subjective measurement unit, and the objective measurement unit can be adjusted. That is, any configuration may be adopted as long as the XYZ directions can be adjusted so that an image calibrated by the calibration optical system 60 is formed on the fundus of the subject eye. For example, a configuration may also be adopted in which the subjective optometry apparatus 1 is moved by providing a configuration in which the subjective optometry apparatus 1 can be moved in the XYZ directions with respect to the chin mount 5. In addition, for example, as a configuration in which the deflection mirror 81 and a measurement unit can be integrally moved in the XYZ directions, a configuration in which adjustment in the XYZ directions can be performed may be adopted. In addition, for example, a configuration may be adopted in which adjustment in the XYZ directions can be performed by only the deflection mirror 81. In this case, examples of the configuration include a configuration in which the deflection mirror 81 is moved in the Z-direction so that the deflection mirror 81 is rotated and a distance between the deflection mirror 81 and the measurement unit is changed. For example, in the alignment control, both subject eyes may be displayed on the monitor 4, and the alignment control of both subject eyes may be performed on the same screen. In addition, for example, in the alignment control, after one subject eye is displayed on the monitor 4 and after the alignment control of one subject eye is completed, the other subject eye may be displayed on the monitor 4, and the alignment control of the other subject eye may be performed. In addition, for example, a configuration may also be adopted in which the alignment control of the other subject eye may be performed based on an alignment control result of one subject eye.

For example, the control section 70 detects a positional deviation of the image of the calibration optical system 60 with respect to the subject eye. For example, the control section 70 controls the driver based on the detected detection result, and optically corrects the position of the image formed by deflecting an apparent luminous flux for guiding the image of the calibration optical system 60 to the subject eye. In this manner, the subjective optometry apparatus 1 in this embodiment has a configuration in which a positional deviation between the subject eye and the calibration optical system is detected and the position of the image formed is optically corrected. Thereby, the positional deviation between the subject eye and the calibration optical system is corrected, and thus it is possible to use the apparatus at an appropriate position and to perform measurement with a high level of accuracy.

<Objective Measurement (S2)>

The control section 70 emits an objective measurement start trigger signal (hereinafter, referred to as a trigger signal) for starting objective measurement (objective measurement) (S2) based on the output of an alignment completion signal. When the trigger signal for starting the objective measurement is emitted, the control section 70 emits a measurement luminous flux from the objective measurement optical system 10. In this case, each measurement luminous flux is reflected by the concave surface mirror 85 through the deflection mirrors 81R and 81L, and is then projected onto the fundus of the subject eye. After measurement light reflected from the fundus is reflected by the deflection mirror 81R (81L) through the concave surface mirror 85, a measurement image is captured by the image capture element 22.

For example, in the measurement of an objective eye refractive power, preliminary measurement of an eye refractive power is first performed, and the display 31 is moved in a direction of the optical axis L2 based on a result of the preliminary measurement, and thus fogging may be applied to the subject eye E. That is, the display 31 may be moved once to a position where the subject eye E is brought into focus. Thereafter, the measurement of the eye refractive power may be performed on the subject eye to which the fogging is applied. In this measurement, a measurement image is captured by the image capture element 22, and an output signal from the image capture element 22 is stored as image data (measurement image) in the memory 72. Thereafter, the control section 70 analyzes a ring image stored in the memory 72 to obtain the value of a refractive power in each longitudinal direction. The control section 70 performs predetermined processing on the refractive power to obtain objective eye refractive powers (objective values) of S (spherical power), C (astigmatic power), and A (astigmatic axis angle) of the examinee's eye during far measurement. The obtained objective values during far measurement are stored in the memory 72.

In the above-described measurement of the objective eye refractive power, the control section 70 may control the correction optical system 90 and may correct optical aberration occurring in the optical path of the objective measurement optical system 10. In this case, the amount of correction based on a refraction power measured by the objective measurement optical system 10 is acquired from the memory 72, and the correction optical system 90 is controlled based on the acquired amount of aberration correction.

More specifically, the amount of correction is set in accordance with the eye refractive power obtained through the preliminary measurement, and the correction optical system 90 is driven based on the set amount of correction. Thereby, this measurement is performed in a state where aberration occurring in the optical path of the objective measurement optical system 10 is corrected, and thus it is possible to measure the objective eye refractive power with a high level of accuracy. In a case where an eye refractive power is consecutively measured (for example, this measurement is performed a plurality of times), the correction optical system 90 may be controlled based on measurement results.

In the above description, the objective eye refractive power has been measured through far measurement. However, the invention is not limited thereto, an objective eye refractive power through near measurement which is an eye refractive power in a state where a visual target is presented at a near measurement distance may be measured. The measurement of the objective eye refractive power may be executed for the right and left eyes at the same time, and may be individually performed for each of the right and left eyes.

<Subjective Measurement (S3)>

Subsequently, subjective measurement (S3) is performed. When the measurement of the objective refractive power is completed and the monitor (in this embodiment, also serves as an operation section) 4 is operated, switching to a subjective far sight measurement (subjective refractive power measurement) mode is performed.

For example, the control section 70 may control the display 31 to display a required visual acuity value visual target on the optical axis L2 (for example, a visual target having a visual acuity value of 0.8). When an initial presentation visual target is presented to the subject eye, the examiner performs far sight measurement of the examinee. When a predetermined switch of the monitor 4 is pressed, a visual acuity value visual target to be presented is switched.

For example, the examiner performs switching to a visual target having a visual acuity value higher by one step in a case where the examinee's answer is a correct answer. On the other hand, the examiner performs switching to a visual target having a visual acuity value lower by one step in a case where the examinee's answer is a wrong answer. That is, the control section 70 may switch a visual target based on a signal for changing a visual acuity value which is received from the monitor 4.

In addition, the examiner may change a calibration power of the calibration optical system 60 by using the monitor 4 to obtain a far measurement subjective value (a spherical power S, an astigmatic power C, and an astigmatic axis angle A) of the subject eye.

The calibration power of the calibration optical system 60 may be set to be a calibration power for each of the right and left eyes, or may be set to be the same calibration power for the right and left eyes. The measurement of a subjective eye refractive power may be performed for the right and left eyes at the same time, or may be individually performed at a timing for each of the right and left eyes. In a case of individual timings, a visual target may not be displayed on the display 31 for a non-measurement eye, and fogging (for example, a fixed refraction power is added to an objective value) may be performed by the calibration optical system 60.

After subjective value is obtained through far measurement, switching to a subjective near sight measurement mode may be performed. When a near measurement mode is set, the control section 70 may control the light projecting optical system 30, may change a convergence angle by the deflection mirror 81, and may present a visual target at a near measurement position. A visual target presenting distance in a near measurement examination may be arbitrarily changed based on an operation signal received from the operation section 4. As a result, the visual target presenting distance is changed from a far measurement position to a near measurement position. In the near measurement examination, a presenting distance of a visual target may be changed at a near measurement position to subjectively obtain an addition and an adjusting power.

In this case, for example, the control section 70 may acquire the amount of aberration correction based on the visual target presenting distance from the memory 72, and may control the correction optical system 90 based on the acquired amount of aberration correction. In addition, in a case where the visual target presenting distance is changed, the control section 70 may change the amount of aberration correction by the correction optical system 90 in accordance with the changed visual target presenting distance. Thereby, even when the visual target presenting distance is changed, the visual target with reduced aberration is presented. In this case, the control section 70 may change the amount of aberration correction in accordance with a calibration power to which the visual target presenting distance is added.

Further, the control section 70 may control a light deflection member in accordance with the change in the presentation position of the visual target, and may change convergence angles of right and left visual target luminous fluxes. In this case, for example, the control section 70 may acquire the amount of aberration correction based on a deflection angle of the light deflection member corresponding to the convergence angle from the memory 72, and may control the correction optical system 90 based on the acquired amount of aberration correction. In addition, in a case where the convergence angle of the visual target luminous flux is changed, the control section 70 may change the amount of aberration correction of the correction optical system 90 in accordance with the changed convergence angle. Thereby, even when the convergence angle is changed, a visual target with reduced aberration is presented.

Similarly to the far measurement examination, in a near measurement examination, for example, the examiner may change a calibration power of the calibration optical system 60 by using a predetermined switch of the operation section 4, and may measure a subjective eye refractive power (near measurement subjective value) in a state where a near measurement visual target is presented. In the near measurement examination, the control section 70 may change the amount of aberration correction of the correction optical system 90 in accordance with the change in calibration power.

<Acquisition of Adjustment Information (S5)>

Here, in this example, the subjective optometry apparatus 1 has a configuration in which objective measurement is performed while subjective measurement is performed, and a change in an optical characteristic of the subject eye is captured. For example, in this example, adjustment information is acquired based on an optical characteristic of the subject eye which is measured by the objective measurement unit while subjective measurement is being performed. For example, the adjustment information can be used to capture a change in the optical characteristic of the subject eye during the execution of the subjective measurement.

Hereinafter, the acquisition of the adjustment information (S5) will be described. For example, in this example, the control section 70 objectively measures an optical characteristic of the subject eye by the objective measurement unit while the optical characteristic of the subject eye is being subjectively measured by the subjective measurement unit (S3).

In more detail, for example, in this example, the control section 70 objectively measures the optical characteristic of the subject eye by the objective measurement unit to acquire a first optical characteristic. For example, the control section 70 objectively measures the optical characteristic of the subject eye by the objective measurement unit to acquire a second optical characteristic while the optical characteristic of the subject eye is being subjectively measured by the subjective measurement unit. The optical characteristic measured by the objective measurement unit may be stored in the memory 72.

For example, in this example, the first optical characteristic is acquired by objectively measuring the optical characteristic of the subject eye by the objective measurement unit before the optical characteristic of the subject eye is subjectively measured by the subjective measurement unit. For example, in this example, the optical characteristic acquired through the objective measurement (S2) performed before the subjective measurement is used as the first optical characteristic (for example, a spherical power, an astigmatic power, and an astigmatic axis angle). Naturally, a configuration may also be adopted in which the first optical characteristic is separately acquired by the objective measurement unit before the optical characteristic of the subject eye is subjectively measured by the subjective measurement unit.

For example, the control section 70 may measure the second optical characteristic when a preset time elapses (for example, in one minute from the start of the subjective measurement, or the like) after the subjective measurement is started. The invention is not limited to a configuration in which the second optical characteristic is acquired when a time which is set as an acquisition timing of the second optical characteristic elapses. The second optical characteristic can be acquired using various configurations as triggers. For example, the acquisition timing of the second optical characteristic may be at least one of a timing when the subjective measurement is started (for example, a state where the projection of a visual target luminous flux is started, a state where an examination program is started, a state where the operation of the operation section of the subjective examination apparatus is started, a state where the driving of the calibration optical system is started, and the like), a timing when an examination visual target is switched, a timing between subjective examinations (a case where a plurality of subjective examinations are performed), and the like. Naturally, a trigger signal for starting the objective measurement may be output at a timing other than the above-described timings.

A plurality of optical characteristics may be acquired while the optical characteristic of the subject eye is being subjectively measured by the subjective measurement unit. In this case, for example, the control section 70 may cause the second optical characteristic to be acquired when a preset time elapses after the subjective measurement is started, and may then cause an optical characteristic (for example, a third optical characteristic, a fourth optical characteristic, and the like) to be acquired whenever a preset time elapses.

For example, the control section 70 acquires adjustment information based on the first optical characteristic and the second optical characteristic. For example, in this example, the control section 70 performs differential processing on the first optical characteristic and the second optical characteristic to acquire the adjustment information. In the following description, a description will be given of an example of a case where a spherical power of an eye refractive power is used as the first optical characteristic and the second optical characteristic. In this example, a spherical power in an eye refractive power has been described as the first optical characteristic and the second optical characteristic, but the invention is not limited thereto. For example, the first optical characteristic and the second optical characteristic are not limited to the eye refractive power. In addition, for example, at least any one of a spherical power, an astigmatic power, and an astigmatic axis angle may be used as the eye refractive power.

In more detail, in this example, for example, the control section 70 acquires adjustment information from a difference between a first eye refractive power acquired before the optical characteristic of the subject eye is subjectively measured by the subjective measurement unit and a second eye refractive power acquired while the optical characteristic of the subject eye is being subjectively measured by the subjective measurement unit. For example, in a case where the spherical power of the first eye refractive power is 1.0 diopter (D) and the spherical power of the second eye refractive power is 3.0 D, the control section 70 performs differential processing to acquire a spherical power of 2.0 D as the adjustment information.

At this time, for example, the control section 70 may correct a measurement result obtained by objectively measuring the subject eye by the objective measurement unit based on calibration information of the calibration optical system. For example, in a case where the subjective optometry apparatus has a configuration in which a measurement luminous flux based on the objective measurement unit passes through the calibration optical system of the subjective measurement unit, a calibration state (arrangement state of an optical member) of the calibration optical system 60 when the first optical characteristic is acquired may be different from a calibration state of the calibration optical system 60 when the second optical characteristic is acquired. For this reason, in a case where the first optical characteristic and the second optical characteristic are compared with each other without considering the calibration state of the calibration optical system, it is difficult to acquire a high-accuracy result as the adjustment information.

In the following description, a description will be given for an example of a case where the first optical characteristic and the second optical characteristic are corrected based on the calibration information of the calibration optical system. In this embodiment, a description will be given of an example of a configuration in which the first optical characteristic and the second optical characteristic are corrected based on the calibration information, but the invention is not limited thereto. For example, the adjustment information may be corrected based on the calibration information.

For example, in this example, the control section 70 corrects the first optical characteristic and the second optical characteristic based on calibration information of the calibration optical system. For example, the control section 70 acquires the calibration information to be used for the correction. For example, the control section 70 evokes calibration information (for example, a spherical power, a cylindrical power, a cylindrical axis) of the calibration optical system during the acquisition of the first optical characteristic from the memory 72. In addition, for example, the control section 70 evokes calibration information (for example, a spherical power, a cylindrical power, a cylindrical axis) of the calibration optical system during the acquisition of the second optical characteristic. The control section 70 may store the calibration information of the calibration optical system during the acquisition of each optical characteristic in the memory 72 in association with each optical characteristic.

For example, the control section 70 evokes first calibration information during the acquisition of the first optical characteristic and second calibration information during the acquisition of the second optical characteristic from the memory 72. For example, the control section 70 may correct the first optical characteristic based on the first calibration information, and may correct the second optical characteristic based on the second calibration information. For example, in a case where a spherical power of the first calibration information is 1.0 D, a spherical power of the second calibration information is 4.0 D, a spherical power of the first optical characteristic is 1.0 D, and a spherical power of the second optical characteristic is 5.0 D, the spherical power of the first optical characteristic in a case where there is no influence of the calibration optical system is set to 0 D, and the spherical power of the second optical characteristic in a case where there is no influence of the calibration optical system is set to 1.0 D. From this, when differential processing is performed on the spherical power of the first optical characteristic and the spherical power of the second optical characteristic in a case where there is no influence of the calibration optical system, 1.0 D is obtained as adjustment information. That is, it can be understood that the spherical power of 1.0 D has changed while the subjective measurement is being performed. In the above-described configuration, a description has been given of an example of a spherical power for the calibration information, but the invention is not limited thereto. For example, at least any one of a spherical power, an astigmatic power, and an astigmatic axis angle may be used as the calibration information.

In a case where the driving of the calibration optical system is not performed (calibration is not performed) when the first optical characteristic is acquired and the driving of the calibration optical system is performed (calibration is performed) only when the second optical characteristic is acquired, only the second optical characteristic is corrected based on the second calibration information, and thus it is possible to acquire adjustment information taking the calibration optical system into consideration. Naturally, in a case where the driving of the calibration optical system is not performed (calibration is not performed) when the second optical characteristic is acquired and the driving of the calibration optical system is performed (calibration is performed) only when the first optical characteristic is acquired, only the first optical characteristic is corrected based on the first calibration information, and thus it is possible to acquire adjustment information taking the calibration optical system into consideration.

In this embodiment, a description has been given of an example of a case where the first optical characteristic and the second optical characteristic are corrected based on calibration information, but the invention is not limited thereto. For example, the adjustment information may be corrected based on the calibration information. In this case, for example, the control section 70 performs differential processing on the first calibration information and the second calibration information to acquire calibration information to be used for the correction. For example, in a case where a spherical power of the first calibration information is 1.0 D, a spherical power of the second calibration information is 4.0 D, a spherical power of the first optical characteristic is 1.0 D, and a spherical power of the second optical characteristic is 5.0 D, calibration information acquired to be used for the correction is set to 3.0 D from a difference between the first calibration information and the second calibration information. In addition, for example, the adjustment information is set to 4.0 D from a difference between the first optical characteristic and the second optical characteristic. For this reason, the adjustment information is corrected based on the calibration information, and thus adjustment information taking the influence of the calibration optical system into consideration is set to 1.0 D.

As described above, a measurement result obtained by objectively measuring the subject eye is corrected based on the calibration information, and thus it is possible to correct a deviation of an optical characteristic which occurs due to the passing of a measurement luminous flux for performing objective measurement through the calibration optical system. Thereby, even when the objective measurement is performed in a case where calibration is performed by the calibration optical system, it is possible to acquire an optical characteristic with a high level of accuracy. For example, particularly, when adjustment information based on at least two optical characteristics acquired through the objective measurement is acquired, it may be difficult to perform comparison due to a deviation occurring between the optical characteristics, and thus this technique is more effective.

<Correction Processing Based on Adjustment Information (S6)>

For example, when adjustment information is acquired, the control section 70 outputs the adjustment information. In this example, for example, the control section 70 transmits the adjustment information to setting controller for setting the amount of correction for correcting a change in an adjustment state. In this embodiment, the control section 70 also serves as the setting controller. Naturally, as a configuration different from the control section 70, a configuration may also be adopted in which a setting controller is separately provided. In this example, as a configuration in which the adjustment information is output, a configuration in which the adjustment information is transmitted to the setting controller has been described as an example, but the invention is not limited thereto. For example, the adjustment information may be displayed on the monitor 4. In addition, for example, the adjustment information may be printed. In this case, the examiner can confirm the adjustment state by confirming the monitor 4 or printed matter.

For example, in this example, the control section 70 sets the amount of correction for correcting a change in the adjustment state of the subject eye which occurs while the optical characteristic of the subject eye is being subjectively measured by the subjective measurement unit, based on the adjustment information. For example, the control section 70 controls the calibration optical system 60 so as to perform correction for canceling the change in the adjustment state of the subject eye which occurs due to the subjective measurement unit, based on the set amount of correction (S6). A configuration in which correction for canceling the change in the adjustment state of the subject eye which occurs due to the subjective measurement unit is not limited to the calibration optical system 60. A configuration may also be adopted in which a different optical system for correction may be separately provided.

For example, the control section 70 sets the amount of correction based on the acquired adjustment state. For example, the control section 70 controls the calibration optical system. For example, regarding the amount of correction, a preset table for each parameter of the adjustment information may be created, and the created table may be stored in a memory (for example, the memory 72). In this case, for example, the control section 70 may evoke the amount of correction corresponding to the adjustment state from the memory 72, and may set the amount of correction. In addition, for example, regarding the amount of correction, a computation expression for deriving the amount of correction for each parameter of the adjustment information may be stored in the memory 72, and the amount of correction may be obtained using the computation expression.

For example, the control section 70 performs correction on a calibration state of the calibration optical system during subjective measurement. For example, the control section 70 performs correction for adding the amount of correction. For example, in a case where a spherical power of the calibration optical system during the subjective measurement is 2.0 D and a spherical power of the adjustment information is 1.0 D, the amount of correction is set to 1.0 D. For example, the control section 70 corrects the spherical power of the calibration optical system 60 based on the amount of correction of 1.0 D. That is, the control section 70 controls the calibration optical system 60 so that the spherical power of the calibration optical system is corrected to 1.0 D.

In this example, a description has been given of an example of a configuration in which correction for canceling the change in the adjustment state of the subject eye is performed based on the adjustment information, but the invention is not limited thereto. For example, it may be determined whether the adjustment information is good or bad based on the adjustment information, and a determination result may be displayed on the monitor 4 or printed matter. In this case, the examiner may confirm the determination result to perform processing based on the determination result. For example, the examiner may perform an operation for improving the adjustment state.

As described above, for example, in this example, the optical characteristic of the subject eye is objectively measured by the objective measurement unit while the optical characteristic of the subject eye is being subjectively measured by the subjective measurement unit, and thus it is possible to confirm a change in the optical characteristic of the subject eye during the subjective measurement. Thereby, the examiner can perform the subjective measurement in consideration of the change in the optical characteristic of the subject eye during the subjective measurement. For this reason, the examiner can measure the optical characteristic of the subject eye with a high level of accuracy when the optical characteristic of the subject eye is subjectively measured.

In addition, for example, in this example, the first optical characteristic is acquired through objective measurement, and the second optical characteristic is acquired through objective measurement while the optical characteristic of the subject eye is being subjectively measured. Adjustment information based on the acquired first optical characteristic and second optical characteristic is acquired, and is output. With such a configuration, it is possible to easily acquire the change in the optical characteristic of the subject eye during the subjective measurement from the adjustment information based on the first optical characteristic and the second optical characteristic of the subject eye. For this reason, the examiner can easily measure the optical characteristic of the subject eye with a high level of accuracy by using the adjustment information when the optical characteristic of the subject eye is subjectively measured.

In addition, for example, in this example, the optical characteristic of the subject eye is objectively measured by the objective measurement unit before the optical characteristic of the subject eye is subjectively measured by the subjective measurement unit. Thereby, the objective measurement is performed before the subjective measurement by the subjective measurement unit, and thus it is possible to acquire an optical characteristic by the objective measurement in a state where a change in the optical characteristic which occurs due to the use of the subjective measurement unit is suppressed. For this reason, it is possible to acquire an optical characteristic through the objective measurement in which the change in the optical characteristic is suppressed, and to acquire better adjustment information.

In addition, for example, in this example, the adjustment information is acquired through comparison processing, and thus it is possible to more easily acquire a change in the optical characteristic of the subject eye during the subjective measurement from the adjustment information having been subjected to the comparison processing. For this reason, the examiner can more easily measure the optical characteristic of the subject eye with a high level of accuracy by using the adjustment information when the optical characteristic of the subject eye is subjectively measured.

In addition, for example, in this example, the amount of correction for correcting the change in the adjustment state of the subject eye is set based on the adjustment information, and correction for canceling the change in the adjustment state of the subject eye which occurs due to the subjective measurement unit is performed based on the amount of correction. Thereby, even when a change in the optical characteristic of the subject eye occurs while the optical characteristic of the subject eye is being subjectively measured by the subjective measurement unit, it is possible to perform measurement in a state where the change in the optical characteristic is canceled. Thereby, it is possible to easily measure the optical characteristic of the subject eye with a high level of accuracy when the optical characteristic of the subject eye is subjectively measured.

<Setting of Initial Value>

For example, in this example, the subjective optometry apparatus 1 may perform objective measurement after the subjective measurement of the optical characteristic of the subject eye is started by the subjective measurement unit, and may set an acquired measurement result as an initial value of the calibration optical system 60 when the optical characteristic of the subject eye is subjectively measured by the subjective measurement unit.

Figure 7:
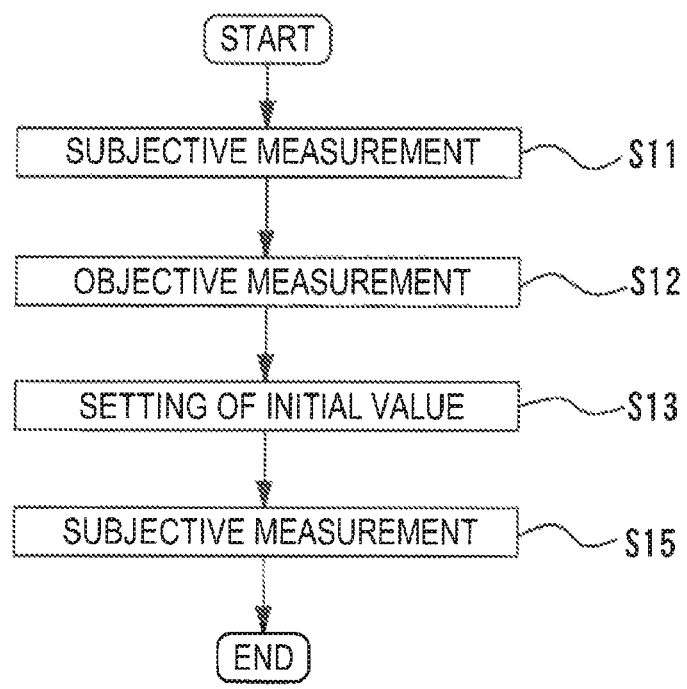
FIG. 7 is a flow chart illustrating a flow of a control operation of the setting of an initial value.

FIG. 7 is a flow chart illustrating a flow of a control operation of the setting of an initial value in this example. Hereinafter, the setting of an initial value will be described. For example, the control section 70 starts subjective measurement (S11). For example, when the monitor (also serves as an operation section in this embodiment) 4 is operated by the examiner, for example, the control section 70 controls the display 31 and displays a required visual acuity value visual target on the optical axis L2.

For example, the control section 70 starts the subjective measurement of the optical characteristic of the subject eye by the subjective measurement unit, and then acquires the optical characteristic of the subject eye by objectively measuring the optical characteristic of the subject eye by the objective measurement unit (S12). For example, in this example, when an initial presentation visual target is presented on the display 31, the control section 70 objectively measures the optical characteristic of the subject eye by the objective measurement unit to acquire the optical characteristic of the subject eye. That is, in this example, as a timing when the subjective measurement is started, a timing when the initial presentation visual target is presented is used. Naturally, the timing when the subjective measurement is started is not limited to the timing when the initial presentation visual target is presented.

For example, the timing when the subjective measurement is started may be a state where the control of the subjective measurement is started. For example, the timing when the subjective measurement is started may be at least any one of a timing when an examination program is started, a timing when the driving of the monitor (also serves as an operation section in this embodiment) 4 and the calibration optical system 60 of the subjective examination apparatus 1 is started, and the like.

For example, the control section 70 sets the optical characteristic of the subject eye which is objectively measured, as an initial value of the calibration optical system 60 when the optical characteristic of the subject eye is subjectively measured by the subjective measurement unit (S13). For example, in this example, as the optical characteristic used for the setting of the initial value, an eye refractive power (for example, a spherical power, an astigmatic power, an astigmatic axis angle) will be described as an example. In this example, as the optical characteristic used for the setting of the initial value, an eye refractive power will be described as an example, but the invention is not limited thereto. For example, the optical characteristic used for the setting of the initial value may be a different optical characteristic. In addition, for example, as the eye refractive power used for the setting of the initial value, at least any one of a spherical power, an astigmatic power, and an astigmatic axis angle may be used.

For example, in this example, the control section 70 sets the optical characteristic of the subject eye which is objectively measured by the objective measurement unit as an initial value of the calibration optical system in subjective measurement (S11) of the optical characteristic of the subject eye which is performed by the subjective measurement unit before the objective measurement is started by the objective measurement unit. The subjective measurement may be continuously performed while the optical characteristic of the subject eye is being acquired by the objective measurement unit. In addition, the subjective measurement may be temporarily stopped while the optical characteristic of the subject eye is being acquired by the objective measurement unit. In this case, an initial value is set, and the control section 70 may restart the subjective measurement. In addition, in this case, after the initial value is set, a switch for starting the subjective measurement is selected by the examiner, and thus the subjective measurement may be restarted.

For example, the control section 70 acquires an eye refractive power of the subject eye by the objective measurement unit. For example, when the control section 70 acquires the eye refractive power of the subject eye, the control section drives the calibration optical system 60 based on the eye refractive power, and sets the eye refractive power as an initial value of a subjective examination. For example, the calibration optical system 60 is controlled by the objective measurement unit so as to calibrate a refractive error of the subject eye based on the eye refractive power of the subject eye.

For example, when the calibration optical system 60 is controlled and the setting of the initial value is completed, the examiner changes a calibration power of the calibration optical system 60 by using the monitor 4 from a state where the setting of the initial value is completed, and obtains a subjective optical characteristic of the subject eye (S15). That is, subjective measurement is performed from the state where the setting of the initial value is completed.

For example, in this example, after the subjective measurement of the optical characteristic of the subject eye is started by the subjective measurement unit, the optical characteristic of the subject eye is acquired by objectively measuring the optical characteristic of the subject eye by the objective measurement unit. The optical characteristic of the subject eye which is objectively measured is set as an initial value of the calibration optical system when the optical characteristic of the subject eye is subjectively measured by the subjective measurement unit. With such a configuration, it is not necessary to wait for the subjective measurement being performed by the subjective examination apparatus until the objective measurement is completed, and thus it is possible to rapidly measure the optical characteristic of the subject eye.

In addition, for example, in this example, the optical characteristic of the subject eye which is objectively measured by the objective measurement unit is set as the initial value of the calibration optical system in the subjective measurement of the optical characteristic of the subject eye which is performed by the subjective measurement unit before the objective measurement is started by the objective measurement unit. With such a configuration, it is possible to rapidly perform the subjective measurement by the subjective examination apparatus.

In this example, a description has been given of an example of a configuration in which the optical characteristic of the subject eye which is objectively measured is set as the initial value of the calibration optical system in the subjective measurement of the optical characteristic of the subject eye which is performed by the subjective measurement unit before the objective measurement is started by the objective measurement unit, but the invention is not limited thereto. For example, the control section 70 performs first subjective measurement for subjectively measuring the optical characteristic of the subject eye by the subjective measurement unit, and then perform second subjective measurement for subjectively measuring the optical characteristic of the subject eye by the subjective measurement unit again. The control section 70 starts the first subjective measurement, and then objectively measures the optical characteristic of the subject eye by the objective measurement unit. The control section 70 sets the optical characteristic of the subject eye which is objectively measured by the objective measurement unit, as an initial value of the second subjective measurement. For example, the first subjective measurement is measurement for acquiring an optical characteristic different from the optical characteristic acquired by the second subjective measurement. In this case, for example, the first subjective measurement may be subjective measurement for subjectively measuring the optical characteristic of the subject eye in a non-calibration state where an optical characteristic of a visual target luminous flux is not changed by the calibration optical system. That is, the first subjective measurement may be a naked eye examination. For example, the second subjective measurement may be subjective measurement for subjectively measuring the optical characteristic of the subject eye by changing the optical characteristic of the visual target luminous flux by the calibration optical system.

For example, in this example, after the first subjective measurement for subjectively measuring the optical characteristic of the subject eye by the subjective measurement unit is performed, the second subjective measurement for subjectively measuring the optical characteristic of the subject eye by the subjective measurement unit is performed again. After the first subjective measurement is started, the optical characteristic of the subject eye is objectively measured by the objective measurement unit, and the optical characteristic of the subject eye which is objectively measured is set as an initial value of the second subjective measurement.

With such a configuration, even when the subjective measurement is performed, an initial value has already been acquired during different subjective measurement, and thus it is possible to rapidly perform the measurement.

What is claimed is:

1. A subjective optometry apparatus that subjectively measures an optical characteristic of a subject eye, the subjective optometry apparatus comprising:
   a light projecting optical system configured to project a visual target luminous flux toward the subject eye;
   a subjective measurement unit configured to subjectively measure the optical characteristic of the subject eye, the subjective measurement unit including a calibration optical system that is disposed in an optical path of the light projecting optical system and is configured to change an optical characteristic of the visual target luminous flux;
   an objective measurement unit for objectively measure an eye refractive power of the subject eye, the objective measurement unit including a measurement optical system configured to emit measurement light to a fundus of the subject eye and receive the measurement light reflected from the subject eye; and
   a controller configured to objectively measure the eye refractive power of the subject eye by the objective measurement unit to acquire a first eye refractive power, and objectively measure the eye refractive power of the subject eye by the objective measurement unit to acquire a second eye refractive power while the optical characteristic of the subject eye is subjectively measured by the subjective measurement unit,
   wherein the subjective optometry apparatus is configured to:
   acquire adjustment information indicating a change in the eye refractive power of the subject eye during the subjective measurement based on the first eye refractive power and the second eye refractive power; and
   output the adjustment information.

2. The subjective optometry apparatus according to claim 1, wherein
   the controller objectively measures the eye refractive power of the subject eye by the objective measurement unit to acquire the first eye refractive power before the subjective measurement unit subjectively measures the optical characteristic of the subject eye.

3. The subjective optometry apparatus according to claim 1, wherein
   the acquisition unit performs differential processing on the first eye refractive power and the second eye refractive power to acquire the adjustment information.

4. The subjective optometry apparatus according to claim 1, wherein the controller is configured to:
   set an amount of correction for correcting, based on the adjustment information, a change in an adjustment state of the subject eye which occurs while the subjective measurement unit subjectively measures the optical characteristic of the subject eye; and
   the subjective optometry apparatus includes a first corrector configured to perform correction for canceling, based on the amount of correction which is set by the setting controller, the change in the adjustment state of the subject eye which occurs due to the subjective measurement unit.

5. The subjective optometry apparatus according to claim 4,
   wherein the calibration optical system as the first corrector.

6. The subjective optometry apparatus according to claim 1,
   wherein the objective measurement unit includes a right subject eye measurement optical system and a left subject eye measurement optical system which are provided as a pair on right and left sides respectively.

7. The subjective optometry apparatus according to claim 1,
   wherein the controller starts the subjective measurement of the optical characteristic of the subject eye by the subjective measurement unit, and then objectively measures the eye refractive power of the subject eye by the objective measurement unit to acquire the eye refractive power of the subject eye, and
   wherein the subjective optometry apparatus further comprises an initial value setting controller configured to set the eye refractive power of the subject eye which is objectively measured by the controller as an initial value for the calibration optical system when the optical characteristic of the subject eye is subjectively measured by the subjective measurement unit.

8. The subjective optometry apparatus according to claim 7,
   wherein the initial value setting controller sets the eye refractive power of the subject eye which is objectively measured by the objective measurement unit as the initial value for the calibration optical system in the subjective measurement of the optical characteristic of the subject eye which is performed by the subjective measurement unit before the objective measurement of the objective measurement unit is started.

9. The subjective optometry apparatus according to claim 7, wherein
   the controller is configured to execute first subjective measurement for subjectively measuring the optical characteristic of the subject eye by the subjective measurement unit and then executing second subjective measurement for subjectively measuring the optical characteristic of the subject eye by the subjective measurement unit, and the controller starts the first subjective measurement and then objectively measures the eye refractive power of the subject eye by the objective measurement unit, and
   the initial value setting controller sets the eye refractive power of the subject eye which is objectively measured by the objective measurement unit as an initial value of the second subjective measurement.

10. The subjective optometry apparatus according to claim 1,
    wherein the calibration optical system is disposed in an optical path of the measurement optical system, and
    wherein the subjective optometry apparatus further comprises second corrector for correcting a measurement result obtained by objectively measuring the subject eye by the objective measurement unit based on calibration information of the calibration optical system.

11. A subjective optometry apparatus for subjectively measuring an optical characteristic of a subject eye, the subjective optometry apparatus comprising:
    a light projecting optical system configured to project a visual target luminous flux toward the subject eye;
    a subjective measurement unit for subjectively measuring the optical characteristic of the subject eye, the subjective measurement unit including a calibration optical system that is disposed in an optical path of the light projecting optical system and is configured to change an optical characteristic of the visual target luminous flux;

an objective measurement unit for objectively measuring the eye refractive power of the subject eye, the objective measurement unit including a measurement optical system configured to emit measurement light to a fundus of the subject eye and receive the measurement light reflected from the subject eye;

a controller for:
  objectively measuring the eye refractive power of the subject eye by the objective measurement unit to acquire a first eye refractive power; and
  objectively measuring the eye refractive power of the subject eye by the objective measurement unit to acquire a second eye refractive power at a timing different from a timing when the first eye refractive power is acquired while the optical characteristic of the subject eye is subjectively measured by the subjective measurement unit;

an acquisition unit for acquiring adjustment information indicating a change in the eye refractive power of the subject eye during the subjective measurement based on the first eye refractive power and the second eye refractive power; and an output unit for outputting the adjustment information.

12. The subjective optometry apparatus according to claim 11,
  wherein the calibration optical system is disposed in an optical path of the measurement optical system, and
  wherein the subjective optometry apparatus further comprises second corrector for correcting a measurement result obtained by objectively measuring the subject eye by the objective measurement unit based on calibration information of the calibration optical system.

13. A non-transitory computer readable recording medium storing a program for a subjective optometry apparatus including a light projecting optical system configured to project a visual target luminous flux toward a subject eye, a subjective measurement unit that is configured to subjectively measure an optical characteristic of the subject eye and includes a calibration optical system that is disposed in an optical path of the light projecting optical system and configured to change an optical characteristic of the visual target luminous flux, and an objective measurement unit that is configured to objectively measure an eye refractive power of the subject eye and includes a measurement optical system that emits measurement light to a fundus of the subject eye and receives the measurement light reflected from the subject eye, and subjectively measuring the optical characteristic of the subject eye, the program being executed by a processor of the subjective optometry apparatus to cause the subjective optometry apparatus to execute:
  a control step of objectively measuring the eye refractive power of the subject eye by the objective measurement unit to acquire a first eye refractive power, and objectively measuring the eye refractive power of the subject eye by the objective measurement unit to acquire a second eye refractive power while the optical characteristic of the subject eye is subjectively measured by the subjective measurement unit
  wherein the subjective optometry apparatus is configured to:
    acquire adjustment information indicating a change in the eye refractive power of the subject eye during the subjective measurement based on the first eye refractive power and the second eye refractive power; and
    output the adjustment information.

* * * * *